(12) United States Patent
Metz et al.

(10) Patent No.: US 10,968,437 B2
(45) Date of Patent: Apr. 6, 2021

(54) FACTORS FOR THE PRODUCTION AND ACCUMULATION OF POLYUNSATURATED FATTY ACIDS (PUFAS) DERIVED FROM PUFA SYNTHASES

(71) Applicant: DSM IP Assets B.V., TE Heelen (NL)

(72) Inventors: James George Metz, Longmont, CO (US); Jerry M. Kuner, Longmont, CO (US); David Glen McCaskill, Greenwood, IN (US); Mendy Louise Foster, Indianapolis, IN (US)

(73) Assignee: DSM IP Assets B.V., Heerlen (NL)

( * ) Notice: Subject to any disclaimer, the term of this patent is extended or adjusted under 35 U.S.C. 154(b) by 0 days.

(21) Appl. No.: 16/107,108

(22) Filed: Aug. 21, 2018

(65) Prior Publication Data

US 2019/0100733 A1 Apr. 4, 2019

Related U.S. Application Data

(62) Division of application No. 15/112,885, filed as application No. PCT/US2015/013274 on Jan. 28, 2015, now Pat. No. 10,087,430.

(60) Provisional application No. 61/932,310, filed on Jan. 28, 2014.

(51) Int. Cl.
| | | |
|---|---|---|
| *C07H 21/04* | (2006.01) |
| *C12N 9/20* | (2006.01) |
| *C12N 15/82* | (2006.01) |
| *C12N 15/79* | (2006.01) |
| *C12N 9/10* | (2006.01) |
| *C12N 9/16* | (2006.01) |
| *A61K 31/202* | (2006.01) |
| *C07K 14/405* | (2006.01) |
| *A23L 33/115* | (2016.01) |
| *C12P 7/64* | (2006.01) |
| *C07K 14/00* | (2006.01) |
| *C07K 14/195* | (2006.01) |

(52) U.S. Cl.
CPC .......... *C12N 9/1029* (2013.01); *A23L 33/115* (2016.08); *A61K 31/202* (2013.01); *C07K 14/00* (2013.01); *C07K 14/405* (2013.01); *C12N 9/16* (2013.01); *C12N 9/20* (2013.01); *C12N 15/79* (2013.01); *C12P 7/6427* (2013.01); *C12Y 301/01* (2013.01); *A23V 2002/00* (2013.01); *C07K 14/195* (2013.01); *C12Y 203/01086* (2013.01)

(58) Field of Classification Search
CPC ....... C12P 7/6427; C12N 15/52; C12N 15/79; C12N 9/20; C12N 9/16; C12Y 101/01; C12Y 203/01041
USPC .... 435/6, 252, 320.1, 134, 419, 252.3, 69.8; 536/23.2
See application file for complete search history.

(56) References Cited

U.S. PATENT DOCUMENTS

2016/0348083 A1* 12/2016 Metz et al.

OTHER PUBLICATIONS

Whisstock et al., Quarterly Reviews of Biophysics 2003, vol. 36 (3): 307-340.*
Devos et al., Proteins: Structure, Function and Genetics, 2000, vol. 41: 98-107.*
Witkowski et al., (Biochemistry 38:11643-11650, 1999.*
Kisselev L., Structure, 2002, vol. 10: 8-9.*

* cited by examiner

*Primary Examiner* — Robert B Mondesi
*Assistant Examiner* — Mohammad Y Meah
(74) *Attorney, Agent, or Firm* — Xi Chen; Shannon McGarrah

(57) ABSTRACT

Factors For the Production and Accumulation of Polyunsaturated Fatty Acids (PUFAs) Derived from PUFA Synthases Abstract Disclosed are novel enhancing factor proteins of the PUFA synthase systems, nucleic acid molecules encoding the same, recombinant nucleic acid molecules and recombinant host cells comprising such nucleic acid molecules, genetically modified microorganisms comprising the same, and methods of making and using the same. Also disclosed are genetically modified microorganisms that have been genetically modified to express a PUFA synthase system for the production of PUFAs, wherein the microorganisms have been modified to express the novel enhancing factor proteins of the PUFA synthase system.

30 Claims, 5 Drawing Sheets

Specification includes a Sequence Listing.

FIG. 3A

```
             (1)1        10        20        30        40        50        60        79
B_TE2   (1) MVMVAEEKRAHEVAVQLYYEDTDFSGFVHHANFLRYFERGRDEMIGLPVIKCLAQDDSSSSSATSIGGGEPPVSLFVH
SzTE2   (1) ---MTAQG---GYRSEMLMYYEDTDLTGAVYAGNYFKYEERARDEAVGIDVLKTLMDKEG----------LALYVR
                                                                              Section2
            (80)80       90       100       110       120       130       140       158
B_TE2  (80) KVHELSFKGRARHGEMLVVRSRVVKESDERLREAHEAWVGN---TLVASGSMDVVFLCGSVDARLVKIPNSVDVALHGYY
SzTE2  (61) KMGEMTFKGGAKHADTLVVESSVEAPSDERLVFKQRASVKDRPETIIVETDVEVVCIDMKTQRVAKIPTQIREALRI---
```

FACTORS FOR THE PRODUCTION AND ACCUMULATION OF POLYUNSATURATED FATTY ACIDS (PUFAS) DERIVED FROM PUFA SYNTHASES

CROSS-REFERENCE TO RELATED APPLICATIONS

This application is a Divisional of U.S. patent application Ser. No. 15/112,885 filed Jul. 20, 2016, which is a National Stage of International Application No. PCT/US2015/013274 filed Jan. 28, 2015, and which claims the benefit of the filing date of United States Provisional Patent Application No. 61/932,310 filed Jan. 28, 2014, the entire contents of each of which are hereby incorporated herein by reference in their entireties.

FIELD OF THE INVENTION

The present invention generally relates to the identification and use of enhancing factor proteins to improve the production of polyunsaturated fatty acids (PUFAs) and particularly, long chain PUFAs (LCPUFAs), in a host organism that has been genetically modified with a PUFA synthase system for producing such PUFAs. The present invention also relates to the organisms that have been genetically modified to express such enhancing factor proteins or modified with respect to such proteins, and to methods of making and using such microorganisms.

BACKGROUND OF THE INVENTION

Polyunsaturated fatty acids (PUFAs) are considered to be useful for nutritional applications, pharmaceutical applications, industrial applications, and other purposes. However, the current supply of PUFAs from natural sources and from chemical synthesis is not sufficient for commercial needs. PUFAs derived from microorganism such as microalgae can be produced in large scale while avoiding the contamination issues associated with fish oils.

Polyketide synthase (PKS) systems are generally known in the art as enzyme complexes related to fatty acid synthase (FAS) systems, but which are often highly modified to produce specialized products that typically show little resemblance to fatty acids. It has now been shown, however, that polyketide synthase-like systems exist in marine bacteria and certain microalgae that are capable of synthesizing polyunsaturated fatty acids (PUFAs) from acetyl-CoA and malonyl-CoA. These systems are referred to herein as PUFA synthases, PUFA synthase systems, PUFA PKS systems, or PKS-like systems for the production of PUFAs, all of which are used interchangeably herein.

The PUFA PKS pathways for PUFA synthesis in *Shewanella* and another marine bacteria, *Vibrio marinus*, are described in detail in U.S. Pat. No. 6,140,486. The PUFA PKS pathways for PUFA synthesis in the eukaryotic Thraustochytrid, *Schizochytrium* sp. ATCC 20888 (hereinafter "*Schizochytrium* 20888"), is described in detail in U.S. Pat. No. 6,566,583. The PUFA PKS pathways for PUFA synthesis in eukaryotes such as members of Thraustochytriales, including the additional description of a PUFA PKS system in *Schizochytrium* 20888 and the identification of a PUFA PKS system in *Thraustochytrium* sp. ATCC 20892, including details regarding uses of these systems, are described in detail in U.S. Pat. No. 7,247,461, and in U.S. Pat. No. 7,642,074, respectively. The PUFA PKS pathways for PUFA synthesis in another eukaryotic Thraustochytrid, *Schizochytrium* sp. ATCC PTA-9695 (hereinafter "*Schizochytrium* 9695"), is described in detail in U.S. Patent Application Publication No. 2010-0266564, published Oct. 21, 2010 and in PCT Publication No. WO 2010/108114, published Mar. 19, 2010. U.S. Pat. No. 7,211,418, discloses the detailed structural description of a PUFA PKS system in *Thraustochytrium* sp. ATCC 20892, and further detail regarding the production of eicosapentaenoic acid (C20:5, n-3) (EPA) and other PUFAs using such systems. U.S. Pat. No. 7,217,856 discloses the structural and functional description of PUFA PKS systems in *Shewanella olleyana* and *Shewanella japonica*, and uses of such systems. These applications also disclose the genetic modification of organisms with the genes comprising the PUFA PKS pathway and the production of PUFAs by such organisms. Furthermore, U.S. Pat. No. 7,776,626 describes a PUFA PKS system in *Ulkenia*, and U.S. Pat. No. 7,208,590 describes PUFA PKS genes and proteins from *Thraustochytrium aureum*. Each of the above-identified applications is incorporated by reference herein in its entirety.

Accordingly, the basic domain structures and sequence characteristics of the PUFA synthase family of enzymes have been described, and it has been demonstrated that PUFA synthase enzymes are capable of de novo synthesis of various PUFAs (e.g., eicosapentaenoic acid (EPA; C20:5, n-3), docosahexaenoic acid (DHA; C22:6, n-3) and docosapentaenoic acid (DPAn-6; C22:5, n-6).

PUFA synthases produce long chain polyunsaturated fatty acids de novo from malonyl-CoA using NADPH (and perhaps NADH) as a reductant. These multi-subunit enzymes have been identified in both marine bacteria and in the eukaryotic Thraustochytrid group of marine algae (Metz et al., 2001, Science 293:290-293). All of the PUFA synthases identified to date contain multiple ACP domains upon which the fatty acids are assembled. ACP domains require attachment of a co-factor by a phosphopantetheinyl transferase (PPTase) in order to function. Individual PPTases can have ACP substrate preferences, and when expressing a PUFA synthase in a heterologous organism, it may be necessary to provide a PPTase that can recognize, and activate, its ACP domains.

Novel production of PUFAs in several heterologous host organisms has been achieved by expression of the genes encoding the PUFA synthase subunits along with an appropriate PPTase. Of particular interest here, is the PUFA synthase derived from *Schizochytrium* 20888 (Metz et al., 2001, Science 293:290-293). The primary products of this PUFA synthase are DHA and DPAn-6. *Schizochytrium* 20888 has been developed as a commercial source for oil enriched in DHA. The organism can accumulate high levels of oil (>60% of the biomass) and DHA can comprise >40% of the fatty acids present in that biomass (Barclay et al., Single Cell Oils, $2^{nd}$ edition. 2010 AOCS Press, pgs 75-96). In the native organism the DHA to DPAn-6 ratio typically ranges between 2.3 to 2.7. Expression of the PUFA synthase subunits of *Schizochytrium* 20888, along with an appropriate PPTase (e.g., HetI from *Nostoc* sp., see Hauvermale et al., 2008, Lipids 41: 739-747 and Metz et al., US Patent Application Publication No. 2013-0150599) in heterologous host cells has resulted in production of DHA and DPAn-6 in those cells. Although DHA and DPAn-6 are produced in cells of *E. coli* (Hauvermale et al., 2008, Lipids 41:739-747), and in yeast and higher plants (Metz et al., US Patent Application Publication No. 2013-0150599), the levels have not approached those observed in the native organism. Additionally, in both yeast and in plants, the DHA to DPAn-6 ratio is typically significantly lower than that observed in the native organism. It is possible that some factor (or factors) in addition to the activated subunits of the enzyme itself is present in the cells of *Schizochytrium* 20888 which facilitates activity of the enzyme.

Since additional factors involved in the PUFA synthesis mechanism can have implications for increasing the efficiency of and/or improving the production of PUFAs in an organism that has been genetically modified to produce such PUFAs, there is a need in the art for finding such factor/factors. Accordingly, there is also a need in the art for improved methods of production of PUFAs, including in microorganisms that have been genetically modified to produce such PUFAs, which take advantage of the activity of such mechanism.

SUMMARY OF THE INVENTION

One embodiment of the invention relates to a recombinant nucleic acid molecule comprising a nucleic acid sequence encoding a polypeptide that is at least 85% identical to an amino acid sequence of SEQ ID NO:1 or SEQ ID NO:3.

In one aspect, the recombinant nucleic acid molecule comprises a nucleic acid sequence encoding a polypeptide that is at least 90% identical to an amino acid sequence of SEQ ID NO:1 or SEQ ID NO:3. In another aspect, the recombinant nucleic acid molecule comprises a nucleic acid sequence encoding a polypeptide that is at least 95% identical to an amino acid sequence of SEQ ID NO:1 or SEQ ID NO:3. In one aspect, the polypeptide enhances the enzymatic activity of a PUFA synthase. In one aspect, the recombinant nucleic acid molecule comprises a nucleic acid sequence encoding a polypeptide that is an enzymatically active fragment of SEQ ID NO:1 or SEQ ID NO:3. In one aspect, the nucleic acid sequence encodes a polypeptide having an amino acid sequence of SEQ ID NO:1 or SEQ ID NO:3. In another aspect, the nucleic acid sequence is SEQ ID NO:5 or SEQ ID NO:7.

Another embodiment of the invention relates to a recombinant nucleic acid molecule comprising a nucleic acid sequence encoding a polypeptide that is at least 85% identical to an amino acid sequence of SEQ ID NO:2 or SEQ ID NO:4.

In one aspect, the recombinant nucleic acid molecule comprises a nucleic acid sequence encoding a polypeptide that is at least 90% identical to an amino acid sequence of SEQ ID NO:2 or SEQ ID NO:4. In another aspect, the recombinant nucleic acid molecule comprises a nucleic acid sequence encoding a polypeptide that is at least 95% identical to an amino acid sequence of SEQ ID NO:2 or SEQ ID NO:4. In one aspect, the polypeptide enhances the enzymatic activity of a PUFA synthase. In one aspect, the recombinant nucleic acid molecule comprises a nucleic acid sequence encoding a polypeptide that is an enzymatically active fragment of SEQ ID NO:2 or SEQ ID NO:4. In one aspect, the nucleic acid sequence encodes a polypeptide having an amino acid sequence of SEQ ID NO:2 or SEQ ID NO:4. In another aspect, the nucleic acid sequence is SEQ ID NO:6 or SEQ ID NO:8.

Another embodiment of the invention relates to an isolated protein encoded by any of the above-described nucleic acid molecules.

Another embodiment of the invention relates to a recombinant nucleic acid molecule comprising any of the above-described nucleic acid molecules, which is operatively linked to an expression control sequence.

Yet another embodiment of the invention relates to a recombinant host cell comprising any of the above-described nucleic acid molecules. In one aspect, this recombinant host cell is a microorganism.

Another embodiment of the invention relates to a genetically modified microorganism, wherein the microorganism has been genetically modified to express any one of the above-described nucleic acid molecules.

In another embodiment, the microorganism has been genetically modified to express one of the above-described recombinant nucleic acid molecules derived from SEQ ID NO:5 or SEQ ID NO:7, and another recombinant nucleic acid molecule derived from SEQ ID NO:6 or SEQ ID NO:8.

In one embodiment, the microorganism endogenously expresses a PUFA synthase system, a phosphopantetheinyl transferase (PPTase), and/or an acyl-CoA synthetase (ACS). In one aspect, the microorganism is a Thraustochytriales microorganism. In one aspect, the microorganism is a *Schizochytrium*. In one aspect, the microorganism is a bacterium.

In another embodiment, the microorganism has been genetically modified to exogenously express a PUFA synthase system, a phosphopantetheinyl transferase (PPTase), and/or an acyl-CoA synthetase (ACS). In one aspect, the microorganism is a Thraustochytriales microorganism. In one aspect, the microorganism is a *Schizochytrium*. In one aspect, the microorganism is a microalga. In one aspect, the microorganism is a yeast. In one aspect, the microorganism is a bacterium. In one aspect, the PUFA synthase comprises at least one functional domain from a PUFA synthase from a microorganism selected from the group consisting of *Schizochytrium* sp. American Type Culture Collection (ATCC) No. 20888, *Schizochytrium* sp. American Type Culture Collection (ATCC) No. PTA-9695, *Thraustochytrium* 23B American Type Culture Collection (ATCC) No. 20892, and a mutant of any of said microorganisms. In one aspect, the PUFA synthase comprises at least one functional domain from a PUFA synthase from a marine bacterium.

In one aspect, the one or more nucleic acid sequences encoding the PUFA synthase of the above-described genetically modified microorganism has been optimized to improve the expression of the PUFA synthase in the microorganism. In one aspect, the genetically modified microorganism comprises at least one polyunsaturated fatty acid (PUFA) selected from the group consisting of: DHA (C22:6, n-3), DPA (C22:5, n-6 or n-3), EPA (C20:5, n-3), ARA (C20:4, n-6), GLA (C18:3, n-6), and/or SDA (C18:4, n-3). In a preferred aspect, the genetically modified microorganism comprises DHA, DPAn-6 and/or EPA.

In one aspect, the amount of DHA, DPAn-6 and/or EPA produced in the above-described genetically modified microorganism, wherein such microorganism is modified to express at least two of the above-described recombinant nucleic acid molecules,—one comprises a nucleic acid sequence encoding a polypeptide that is at least 90% identical to an amino acid sequence of SEQ ID NO:1 or SEQ ID NO:3, and another comprises a nucleic acid sequence encoding a polypeptide that is at least 90% identical to an amino acid sequence of SEQ ID NO:2 or SEQ ID NO:4, is higher than that is produced in the counterpart microorganism which none of the above-described recombinant nucleic acid molecule is expressed.

In one aspect, the ratio of DHA:DPAn-6 produced in the above-described genetically modified microorganism, wherein such microorganism is modified to express at least two of the above-described recombinant nucleic acid molecules,—one comprises a nucleic acid sequence encoding a polypeptide that is at least 90% identical to an amino acid sequence of SEQ ID NO:1 or SEQ ID NO:3, and another comprises a nucleic acid sequence encoding a polypeptide that is at least 90% identical to an amino acid sequence of SEQ ID NO:2 or SEQ ID NO:4, is higher than that is produced in the counterpart microorganism which none of the above-described recombinant nucleic acid molecule is expressed.

In one aspect, the microorganism is a microalga, a yeast, or a bacterium.

In another embodiment, the invention provides a genetically modified microorganism, wherein the microorganism has been genetically modified to delete or inactivate one of the above-described recombinant nucleic acid molecules expressed by the microorganism. In one aspect, the microorganism is a Thraustochytriales microorganism. In one aspect, the microorganism is a *Schizochytrium*.

In one embodiment, the invention provides an oil obtained from one of the above-described genetically modified microorganism.

In one embodiment, the invention provides a method to produce an oil comprising at least one polyunsaturated fatty acid (PUFA), comprising growing one of the above-described genetically modified microorganism.

In one embodiment, the invention provides an oil produced by the above-described method. In one aspect, the oil contains at least one polyunsaturated fatty acid (PUFA) selected from the group consisting of: DHA (C22:6, n-3), DPA (C22:5, n-6 or n-3), and/or EPA (C20:5, n-3).

In one embodiment, the invention provides a food product or feed product that contains the above-described oil or genetically modified microorganisms.

In one embodiment, the invention provides a pharmaceutical product that contains the above-described oil.

In one embodiment, the invention provides a method to produce an oil comprising at least one PUFA, comprising recovering an oil from one of the above-described genetically modified microorganisms.

In one embodiment, the invention provides a method to produce at least one polyunsaturated fatty acid (PUFA), comprising growing the above-described genetically modified microorganisms.

In one embodiment, the invention provides a method to produce at least one polyunsaturated fatty acid (PUFA), comprising obtaining or recovering the PUFA from one of the above-described genetically modified microorganisms.

In one embodiment, the invention provides a method to provide a supplement or therapeutic product containing at least one PUFA to an individual, comprising providing to the individual the above-described genetically modified microorganisms, oil, food products, or pharmaceutical products.

In one embodiment, the invention provides a process for transforming a microorganism to express PUFAs, comprising transforming a microorganism with nucleic acid molecules encoding a PUFA synthase, with a nucleic acid molecule encoding a phosphopantetheinyl transferase (PPTase), with a nucleic acid molecule encoding an acyl-CoA synthetase (ACS), and with at least one of the above-described nucleic acid molecules.

BRIEF DESCRIPTION OF THE DRAWINGS OF THE INVENTION

FIG. 3A is a diagram showing the alignment between the amino acid sequence of enhancing factor proteins B-TE2 and Sz-TE2.

SEQUENCE LISTING

Figure 1:
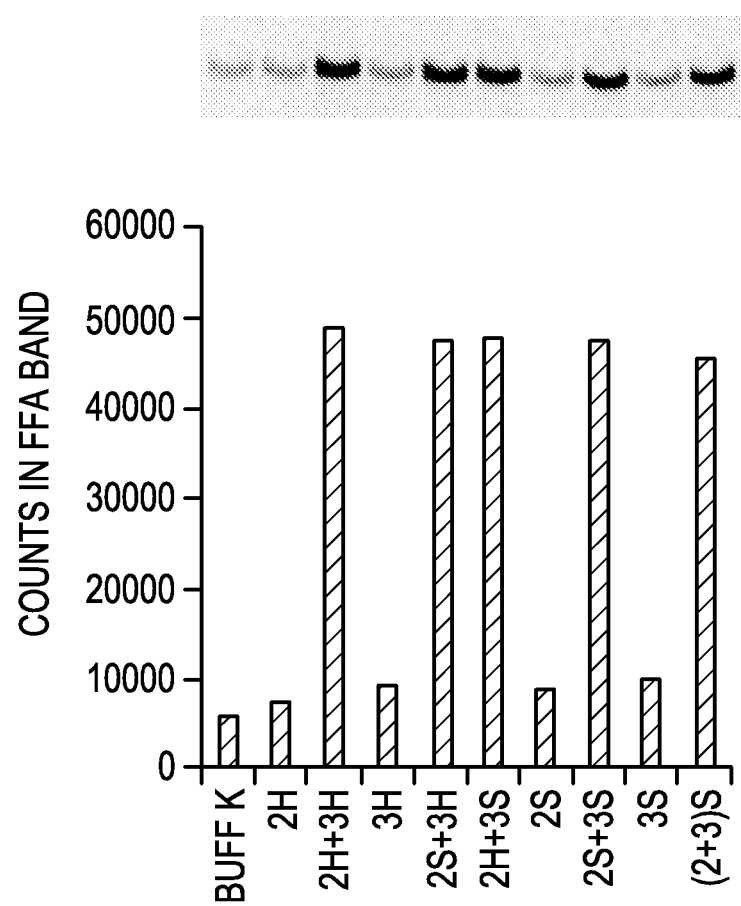
FIG. 1 is a diagram showing the result of an in vitro PUFA synthase activity enhancing assay using enhancing factor proteins Sz-TE2 and Sz-TE3 expressed in *E. coli*.

The nucleic acid sequences and deduced amino acid translation sequences listed in the accompanying sequence listing are shown using standard letter abbreviations for nucleotide bases and amino acids, as defined in 37 C.F.R. § 1.822. Only one strand of each nucleic acid sequence is shown, but the complementary strand is understood to be included by any reference to the displayed strand. In the accompanying sequence listing:

SEQ ID NO:1 shows the amino acid of the TE2 protein from *Schizochytrium* sp. ATCC-20888 (Sz-TE2):

```
  1  MTAQGGYRSE MLMYYEDTDL TGAVYAGNYF KYFERARDEA VGIDVLKTLM DKEGLALYVR

61  KMGEMTFKGG AKHADTLVVE SSVEAPSDFR LVFKQRASVK DRPETIIVET DVEVVCIDMK

121  TQRVAKIPTQ IREALRI
```

SEQ ID NO:2 shows the amino acid sequence of the TE3 protein from *Schizochytrium* sp. ATCC 20888 (Sz-TE3):

```
  1  MAAPSTAVCG ELPKLDEAPL KVSRARGYDA LDVKVYREDT DTVGIVFYRN FLTWFERGRE
 61  NAISTDFLAG LFEYSGDSFV VTRSEQSFRK PAFYGDELEV RTIPFADGPF RLHFDQSIWR
121  KSDNTLLVAG FVEMVTVSRT FQLTKVPQPV HDLIYYFDDC KSNFTYCEKPGAKKRPLRRK
181  PGAPSSLGKT TELDLVIHLA DTDFTGIAFH PNYYCWFERA RSDFLSNEIL ARAKTEFHAV
241  PVVRSAKLAY KNGARPVEPL RITTTQDPKG EHSDFVVPIL QKLTRVSNDQ TLVEAVFEMC
301  FVHDKERHLV KVPSIVRDAI A
```

SEQ ID NO:3 shows the amino acid sequence of the TE2 protein from *Schizochytrium* sp. ATCC PTA-9695 (B-TE2):

```
  1  MVMVAEEKRA HEVAVQLYYE DTDFSGFVHH ANFLRYFERG RDEMIGLPVL KCLAQDDSSS
 61  SSSATSIGGG EPPVSLFVHK VHELSFKGRA RHGEMLVVRS RVVKESDFRL RFAHEAWVGN
121  TLVASGSMDV VFLCGSVDAR LVKIPNSVDV ALHGYY
```

SEQ ID NO:4 shows the amino acid sequence of the TE3 protein from *Schizochytrium* sp. ATCC PTA-9695 (B-TE3):

```
  1  MRIDEEAIRV AAARGYDALP VTVYREFTDC LGIVFYRHYL AWFERGRENV ISVQFLADLF
 61  RETGESFVVT RSEQVFKRSA RYGDQLEVRT IPFLDGDYRL GFDQSVWHGN EMLVHGFVEM
121  VCVSKSFQLA QQPALVRKLI GCFDECTRNF TYVGTKARMP QTIRRRRGTA SLPQAQKPLV
181  FDGLHLHQAD TDFTGITFHP NYYCYFERAR SQALTPAVLA NVAEFANAVP VIRQARMTFK
241  QGARAYETLR VLTSIALDDS GGSSSSSNKY VVPFEQVLVR REDDKVLVEA RIEIVFVDQT
301  TKLPCPIPDA VAAKMQELFA V
```

SEQ ID NO:5 shows the nucleotide sequence encoding the TE2 protein from *Schizochytrium* sp. ATCC 20888 (SEQ ID NO:1):

```
  1  atgacggcgc agggcggcta cagatcggag atgctcatgt actatgagga cacggacctg
 61  accggagccg tctatgcggg caactacttc aagtactttg agcgcgcgcg cgacgaggct
121  gtgggcatcg atgtcctcaa gacgctcatg gacaaggagg gcctggcttt gtacgtgcgc
181  aaaatgggcg agatgacctt taaggaggc gccaagcacg ccgacacgct cgtcgtcgag
241  tcctctgtcg aggctccctc ggactttcgc cttgtgttca agcagcgggc atccgtcaag
301  gaccgtcccg agacgatcat tgtcgagacc gatgttgagg tcgtttgcat cgacatgaaa
361  acgcagcgtg tcgccaagat cccgacgcaa atccgggaag cacttcgtat c
```

SEQ ID NO:6 shows the nucleotide sequence encoding the TE3 protein from *Schizochytrium* sp. ATCC 20888 (SEQ ID NO:2):

```
  1  atggctgcgc catcgactgc agtctgcggc gagctgccaa agctcgacga ggcgcctctc
 61  aaggtgtctc gtgcacgtgg ctacgacgcg ctcgacgtca aggtgtacag agaggacaca
121  gacacagtag ggatcgtgtt ctatcgtaac ttttttgacct ggtttgagcg tggccgggaa
181  aacgcgatct ccacagactt tctcgcagga ctgttcgagt acagtggtga ctccttcgtg
241  gtcacgcggt ccgagcagtc gtttcgcaag cctgcatttt acggcgatga actcgaagtc
```

-continued

```
301  cgaaccattc cttttgcaga tgggccctttt cgcctgcact ttgaccagag catctggcga
361  aagagcgaca acacattgct agtcgctggc tttgtagaga tggtcacggt gagcagaact
421  tttcagctca ccaaggtacc tcagccggtg cacgacctca tttattactt tgacgattgc
481  aagtcgaact tcacctactg cgaaaagccc ggcgccaaga aaaggccgct tcggcgtaag
541  cccggggcgc cctcttcact tggcaaaacc acagagcttg acctggtcat tcacttggcc
601  gacactgact ttactggaat cgcattccac cccaactact actgttggtt cgagcgtgcg
661  cgctcggatt ttctcagcaa tgagattctt gcacgcgcca agaccgagtt tcatgctgtt
721  cccgttgtgc gcagtgcaaa actcgcgtac aaaaacggcg cgaggcctgt tgagccgctc
781  cgcattacaa cgacgcaaga tccgaaggc gagcactcgg actttgtcgt accgattctt
841  caaaagctta cgcgtgtctc gaacgaccag acgctcgtcg aagccgtctt tgagatgtgc
901  tttgttcatg acaaggagcg ccacctcgtc aaggtcccgt cgatcgttcg cgatgctatt
961  gcg
```

SEQ ID NO:7 shows the nucleotide sequence encoding the TE2 protein from *Schizochytrium* sp. ATCC PTA-9695 (SEQ ID NO:3):

```
  1  atggtcatgg tcgcggagga gaagagggcg cacgaggtgg cagtacagtt gtactatgag
 61  gacacggact tctccggctt tgtccatcat gccaacttcc tgcgctactt tgaacgcggc
121  cgggatgaga tgattggcct gcccgttctc aaatgcttgg cccaagacga tagctcttct
181  tcttcttctg caacttcaat tggtggtggc gagcctccag tatcattgtt cgtgcataag
241  gtgcacgagt tgtcgttcaa aggtcgcgct cggcacggtg agatgctcgt ggtgcggtca
301  cgagtggtca aggaatcgga cttccgactg cgctttgcac acgaagcgtg ggtggggaac
361  acgctcgtgg cctctggatc aatggacgtg tgttcctgt gtggctcggt cgatgcgcga
421  ttagtgaaga tccctaactc ggtcgatgtg gccttgcacg gatactat
```

SEQ ID NO:8 shows the nucleotide sequence encoding the TE3 protein from *Schizochytrium* sp. ATCC PTA-9695 (SEQ ID NO:4):

```
  1  atgagaatcg acgaggaggc gatacgcgtg gcagcggcgc gcgggtacga cgccttgccc
 61  gtgacagtgt atcgagagtt taccgactgc ctgggcattg tgttctaccg gcactaccta
121  gcgtggtttg agcgcgggcg cgagaacgtc atctcggtgc agttcttggc ggatctgttt
181  cgcgaaacgg gggagtcgtt cgtggtgacg cgctccgagc aagtgtttaa gcgctcagcg
241  cgctatggcg accaactcga agtgcgcacc attcctttcc tggacggcga ctaccgcctc
301  ggcttcgacc agagcgtgtg gcacggcaat gagatgctcg tgcatggctt cgtggagatg
361  gtctgcgtaa gcaagagctt ccagctggcg caacaaccgg cgctcgtgcg caagctgatc
421  ggctgctttg acgagtgcac gcgcaacttc acctacgtcg gcaccaaggc ccgcatgccc
481  caaccattc gacgacgcag aggcacggcc agtctaccac aagcacagaa gcctctagtg
541  tttgacgggc tgcacttgca ccaagcggac acagacttca caggtatcac ttttcacccc
601  aactactact gctactttga acgcgcgcgc tcgcaggcat tgactcccgc cgtattagcg
661  aacgtggctg agttcgccaa cgctgtgcca gtcatccgcc aagcccgcat gaccttcaag
721  caaggcgcga gagcgtacga gacactccgc gtgctcacat caattgctct ggatgatagc
781  ggcggcagca gcagcagcag caacaagtat gtcgtgccgt ttgagcaggt gctcgtgcga
```

```
-continued
841  agagaagacg acaaggtgct ggtggaggcg cgaatcgaga ttgtctttgt ggaccagact 901  acgaagttgc cctgcccgat tcctgacgca gtggcagcca agatgcagga gttgtttgcg 961  gta
```

DETAILED DESCRIPTION OF THE INVENTION

Abbreviations:
  ACS acyl-CoA synthetase
  B-TE2 or B_TE2 PUFA synthase activity enhancing factor 2 protein from Schizochytrium 9695
  B-TE3 or B_TE3 PUFA synthase activity enhancing factor 3 protein from Schizochytrium 9695
  DHA docosahexaenoic acid
  DPAn-6 docosapentaenoic acid n-6
  EF-X PUFA synthase in vitro activity enhancing factor proteins
  EPA eicosapentaenoic acid
  FAME fatty acid methyl ester
  FAS fatty acid synthase
  HPLC high-performance liquid chromatography
  KO knock-out
  LCPUFA long chain polyunsaturated fatty acid
  PKS polyketide synthase
  PPTase phosphopantetheinyl transferase
  PUFA polyunsaturated fatty acid
  Sz-TE2 or SzTE2 PUFA synthase activity enhancing factor 2 protein from Schizochytrium 20888
  Sz-TE3 or SzTE3 PUFA synthase activity enhancing factor 3 protein from Schizochytrium 20888
  Schizochytrium 9695 Schizochytrium sp. strain ATCC PTA-9695
  Schizochytrium 20888 Schizochytrium sp. strain ATCC 20888

The present invention generally relates to the provision of proteins (generally referred to herein as "PUFA synthase in vitro activity enhancing factor proteins" or "EF-X"), and nucleic acid molecules encoding such proteins, for the improvement of the production of polyunsaturated fatty acids (PUFAs) and particularly, long chain PUFAs (LCPU-FAs), in a host organism that has been genetically modified to produce such PUFAs. The present invention also relates to the organisms that have been genetically modified to express certain of such proteins, and to methods of making and using such proteins and organisms.

According to the present invention, an organism that has been genetically modified to express a PUFA synthase system, wherein the organism does not naturally (endogenously, without genetic modification) express such a system, can be referred to herein as a "heterologous" host organism with regard to the modification of the organism with the PUFA synthase system. The genetic modifications of the present invention may also be used to improve PUFA production in a host organism that endogenously expresses a PUFA synthase system, where the organism is not further modified with a different PUFA synthase system or a portion thereof, but is genetically modified to express the enhancing factor proteins described herein.

More particularly, the present inventors have discovered and disclose for the first time a class of enhancing factor proteins which enhance the activity of PUFA synthases. The present inventors have determined that an endogenous producer of PUFA by the PUFA synthase system, i.e., Schizochytrium 20888, possesses one or more enhancing factor proteins that may be capable to enhance the production of PUFAs. This is evident by the fact that the expression of these factors, especially co-expression of the two of such enhancing factor proteins in heterologous host organisms that are also expressing an active PUFA synthase system from Schizochytrium 20888 results in increased accumulation of PUFAs and increased ratio of DHA:DPAn-6 in the cells of those organisms. Disruption of the endogenous genes encoding these proteins in Schizochytrium 20888 leads to a decrease in accumulation of PUFAs in those cells.

The present inventors have identified from Schizochytrium 20888 two enhancing factor proteins: SEQ ID NO:1 and SEQ ID NO:2. They are not part of the PUFA synthase system itself but were found to enhance the in vitro activity of PUFA synthases. Both of the enhancing factor proteins have homology to a class of thioesterases called 4-hydroxybenzoyl-CoA-like thioesterases. However, the enhancing factor proteins may or may not have thioesterase activity. SEQ ID NO:1 (referred to herein as the enhancing factor 2 protein from Schizochytrium 20888, or Sz-TE2 protein) has one thioesterase domain, while SEQ ID NO:2 (referred to herein as the enhancing factor 3 protein from Schizochytrium 20888, or Sz-TE3 protein) has two thioesterase domains. The Sz-TE2 protein and the Sz-TE3 protein function most efficiently when they are expressed together. See, for example, Example 4.

Homologs of these two proteins have also been identified in another Thraustochytrid—Schizochytrium sp. strain ATCC PTA-9695 which is referred to here as 'Schizochytrium 9695'. SEQ ID NO:3 is referred to herein as the enhancing factor 2 protein from Schizochytrium 9695 (referred to herein as B-TE2 protein). SEQ ID NO:4 is referred to herein as the enhancing factor 3 protein from Schizochytrium 9695 (referred to herein as B-TE3 protein). These homologs were shown in the present invention to have in vitro PUFA synthase enhancing activity that is similar to the homolog proteins from Schizochytrium 20888. See, for example, Examples 9 and 10.

Sz-TE2 and B-TE2 are referred to herein in general as TE2 enhancing factor proteins. Sz-TE3 and B-TE3 are referred to herein in general as TE3 enhancing factor proteins. It was discovered in the present invention that TE2, TE3, and in particular, the combination of TE2 and TE3, enhance the enzymatic activity of PUFA synthase in a host cell where TE2 and TE3 are exogenously expressed.

Thioesterases are a class of enzymes which have been extensively studied in the past. A polypeptide or a domain of a polypeptide having thioesterase activity has been previously shown to be capable of catalyzing the hydrolysis of the thioester bond of fatty acids bound to CoA or acyl carrier proteins. Members of thioesterase enzymes have been classified into families by primary structure and into clans and superfamilies by tertiary structure (see Cantu et al., 2010, Protein Science, 19:1281-1295). More than eighty crystal structures of thioesterases or their domains are available, which provide a wealth of information on the tertiary structures, catalytic residues, and mechanisms of the enzymes. ibid. Some thioesterases have the feature of a hot dog fold (see Pidugu et al., 2009, BMC Structural Biology, 9:37 ppl-16). The hotdog fold was first identified in the crystal structure of β-hydroxydecanoyl thioester dehydratase (Fab A) from *E. coli* (see Leesong et al., 1996, Structure 4(3):253-264). According to Leesong et al., at least eight types of hotdog fold thioesterases have been identified and their crystal structures were made available, including 4-hydroxybenzoyl-CoA thioesterase. Among the subfamilies of thioesterase, the subfamily of 4-hydroxybenzoyl-CoA thioesterases shares the closest protein sequence homology to the TE2 and TE3 proteins identified in the present invention.

The present inventors believe that the enhancing factor proteins discovered by the present inventors are useful for modifying PUFA accumulation in hosts expressing a PUFA synthase, i.e., increasing or decreasing the amount of the PUFA accumulation and/or changing the ratio of the PUFA products. Indeed, the Examples presented herein demonstrate that the enhancing factor proteins from *Schizochytrium* 20888 increase the accumulation of PUFAs in those *E. coli* and yeast strains which have been genetically modified with a *Schizochytrium* 20888 PUFA synthase system. In addition, the enhancing factor proteins alter the ratio of the PUFA products of the PUFA synthase system. Each of these enhancing factor proteins and the nucleic acids encoding the same are encompassed by the present invention, as well as homologues and biologically active fragments thereof. These proteins and nucleic acid molecules will be discussed in detail below and in the Examples.

One embodiment of the present invention relates to isolated enhancing factor proteins that enhance the amount and alter the ratio of the products of a PUFA synthase system. In one aspect of the invention, the isolated enhancing factor protein(s) is (are) derived from an organism that endogenously expresses a PUFA synthase system. Such organisms include, but are not limited to, members of the Thraustochytriales. In one aspect, the isolated proteins are derived from the genus *Schizochytrium*. In another aspect, the isolated enhancing factor protein is derived from *Schizochytrium* 20888 or from *Schizochytrium* 9695. In another aspect, any protein that is a homolog of the enhancing factor proteins identified in the present invention and that functions in conjunction with any PUFA synthase system to modify the production and/or accumulation of PUFAs in a host cell or organism can be used in the present invention. The invention is not limited to those specific examples described herein.

In another aspect, the isolated enhancing factor protein is encoded by a nucleotide sequence selected from any one of SEQ ID NOs: 5, 6, 7, or 8. In another aspect, the isolated enhancing factor protein is encoded by a degenerate nucleic acid sequence encoding a protein that is encoded by a nucleotide sequence selected from any one of SEQ ID NOs: 5, 6, 7, or 8. SEQ ID NO:5 is the nucleotide sequence encoding the TE2 protein from *Schizochytrium* 20888. SEQ ID NO:6 is the nucleotide sequence encoding the TE3 protein from *Schizochytrium* 20888. SEQ ID NO:7 is the nucleotide sequence encoding the TE2 protein from *Schizochytrium* 9695. SEQ ID NO:8 is the nucleotide sequence encoding the TE3 protein from *Schizochytrium* 9695.

In yet another aspect, the isolated enhancing factor protein comprises an amino acid sequence selected from any one of SEQ ID NOs:1, 2, 3, 4, or a homologue of any of such amino acid sequences, including any biologically active fragments or domains of such sequences.

In some embodiment, an enhancing factor protein of the present invention includes, for example and without limitation, at least one protein comprising an amino acid sequence having at least 50% (e.g., at least 55%; at least 60%; at least 65%; at least 70%; at least 75%; at least 80%; at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; at least 99%) identity to the amino acid sequence of SEQ ID NO:1 or SEQ ID NO:3.

In some embodiment, an enhancing factor protein includes, for example and without limitation, at least one protein comprising an amino acid sequence having at least 50% (e.g., at least 55%; at least 60%; at least 65%; at least 70%; at least 75%; at least 80%; at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; at least 99%) identity to the amino acid sequence of SEQ ID NO:2 or SEQ ID NO:4.

One embodiment of the invention relates to an isolated nucleic acid molecule comprising a nucleic acid sequence encoding a polypeptide that is at least 50% (e.g., at least 55%; at least 60%; at least 65%; at least 70%; at least 75%; at least 80%; at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; at least 99%) identity to the amino acid sequence of SEQ ID NO:1 or SEQ ID NO:3. In one aspect, the polypeptide enhances the enzymatic activity of a PUFA synthase. In one aspect, the isolated nucleic acid molecule comprising a nucleic acid sequence encodes a polypeptide having an amino acid sequence of SEQ ID NO:1 or SEQ ID NO:3. In one aspect, the isolated nucleic acid molecule comprises a nucleic acid sequence which is SEQ ID NO:5 or SEQ ID NO:7.

One embodiment of the invention relates to an isolated nucleic acid molecule comprising a nucleic acid sequence encoding a polypeptide that is at least 50% (e.g., at least 55%; at least 60%; at least 65%; at least 70%; at least 75%; at least 80%; at least 81%; at least 82%; at least 83%; at least 84%; at least 85%; at least 86%; at least 87%; at least 88%; at least 89%; at least 90%; at least 91%; at least 92%; at least 93%; at least 94%; at least 95%; at least 96%; at least 97%; at least 98%; at least 99%) identity to the amino acid sequence of SEQ ID NO:2 or SEQ ID NO:4. In one aspect, the polypeptide enhances the enzymatic activity of a PUFA synthase. In one aspect, the isolated nucleic acid molecule comprising a nucleic acid sequence encodes a polypeptide having an amino acid sequence of SEQ ID NO:2 or SEQ ID NO:4. In one aspect, the isolated nucleic acid molecule comprises a nucleic acid sequence which is SEQ ID NO:6 or SEQ ID NO:8.

The invention includes the expression of one or more enhancing factor proteins as described and exemplified herein with a PUFA synthase system as described herein and with an exogenous PPTase and/or acyl-CoA synthetase (ACS) to increase PUFA production and/or accumulation in a heterologous host.

PUFA Synthase Systems (PUFA PKS Systems)

Accordingly, the present invention is directed to the enhancing factor proteins for use in connection with a PUFA synthase systems. As used herein, a PUFA synthase system (which may also be referred to as a PUFA PKS system, PUFA synthase PKS-like system, PUFA synthase, or PUFA synthase enzyme) generally has the following identifying features: (1) it produces PUFAs, and particularly, long chain PUFAs, as a natural product of the system; and (2) it produces those PUFAs de novo using malonyl-CoA as the carbon source. In addition, the ACP domains present in the PUFA synthase enzymes require activation by attachment of a cofactor (4-phosphopantetheine). Attachment of this cofactor is carried out by phosphopantetheinyl transferases (PPTase). If the endogenous PPTases of the host organism are incapable of activating the PUFA synthase ACP domains, then it is necessary to provide a PPTase that is capable of carrying out that function. The HetI enzyme of *Nostoc* sp. is an exemplary and suitable PPTase for activating PUFA synthase ACP domains. Reference to a PUFA synthase system refers collectively to all of the genes and their encoded products that work together to produce PUFAs in an organism.

More specifically, a PUFA synthase system as referenced herein produces polyunsaturated fatty acids (PUFAs) and particularly, long chain PUFAs (LCPUFAs), as products. For example, an organism that endogenously (naturally) contains a PUFA synthase system makes PUFAs using this system. According to the present invention, PUFAs are fatty acids with a carbon chain length of at least 16 carbons, and more preferably at least 18 carbons, and more preferably at least 20 carbons, and more preferably 22 or more carbons, with at least 3 or more double bonds, and preferably 4 or more, and more preferably 5 or more, and even more preferably 6 or more double bonds, wherein all double bonds are in the cis configuration. Reference to long chain polyunsaturated fatty acids (LCPUFAs) herein more particularly refers to fatty acids of 18 and more carbon chain length, and preferably 20 and more carbon chain length, containing 3 or more double bonds. LCPUFAs of the omega-6 series include: gamma-linolenic acid (C18:3), di-homo-gamma-linolenic acid (C20:3, n-6), arachidonic acid (C20:4, n-6), adrenic acid (also called docosatetraenoic acid or DTA) (C22:4, n-6), and docosapentaenoic acid (C22:5, n-6). The LCPUFAs of the omega-3 series include: alpha-linolenic acid (C18:3), eicosatrienoic acid (C20:3, n-3), eicosatetraenoic acid (C20:4, n-3), eicosapentaenoic acid (C20:5, n-3), docosapentaenoic acid (C22:5, n-3), and docosahexaenoic acid (C22:6, n-3). The LCPUFAs also include fatty acids with greater than 22 carbons and 4 or more double bonds including but not limited to C28:8, n-3.

The enhancing factor proteins according to the present invention can be used in connection with a PUFA synthase system from either a prokaryotic organism or an eukaryotic organism. Description of the PUFA synthase systems of various organisms can be found, for example, in U.S. Pat. Nos. 6,140,486; 6,566,583; Metz et al., *Science* 293:290-293 (2001); U.S. Pat. Nos. 7,247,461; 7,211,418; 7,217,856, U.S. Patent Application Publication No. 2010-0266564, and PCT Publication No. WO 2006/135866.

The domain architecture of various PUFA synthase systems from marine bacteria and members of *Thraustochytrium*, and the structural and functional characteristics of genes and proteins comprising such PUFA synthase systems, have been described in detail (see, e.g., U.S. Pat. Nos. 6,140,486; 6,566,583; Metz et al., Science 293:290-293 (2001); U.S. Pat. Nos. 7,247,461; 7,211,418; 7,217,856, U.S. Patent Application Publication No. 2010-0266564, and PCT Publication No. WO 2006/135866).

The enzymatic activity of a PUFA synthase can be measured in the form of PUFA accumulation rate and PUFA composition profile. Two exemplary methods for measuring the activity of PUFA synthase are described in Example 1 of the present application. In those assays, radio labeled malonyl CoA is used as substrate and is converted into PUFAs by the PUFA synthase system. The amount and compositions of PUFAs produced are measured.

Phosphopantetheinyl Transferase (PPTase)

As discussed under the general guidelines for the production of PUFAs in a heterologous host above, in order to produce PUFAs, a PUFA synthase system must work with an accessory protein that transfers a 4'-phosphopantetheinyl moiety from coenzyme A to the acyl carrier protein (ACP) domain(s). Therefore, a PUFA synthase system can be considered to include at least one 4'-phosphopantetheinyl transferase (PPTase) domain, or such a domain can be considered to be an accessory domain or protein to the PUFA synthase system. Structural and functional characteristics of PPTases have been described in detail, for example, in U.S. Pat. Nos. 7,247,461; 7,211,418; and 7,217,856.

According to the present invention, a domain or protein having 4'-phosphopantetheinyl transferase (PPTase) biological activity (function) is characterized as the enzyme that transfers a 4'-phosphopantetheinyl moiety from Coenzyme A to the acyl carrier protein (ACP). This transfer to an invariant serine reside of the ACP activates the inactive apo-form to the holo-form. In both polyketide and fatty acid synthesis, the phosphopantetheine group forms thioesters with the growing acyl chains. The PPTases are a family of enzymes that have been well characterized in fatty acid synthesis, polyketide synthesis, and non-ribosomal peptide synthesis. The sequences of many PPTases are known, and crystal structures have been determined (e.g., Reuter et al., 1999, EMBO J. 18(23):6823-6831) as well as mutational analysis of amino acid residues important for activity (Mofid et al., 2004, Biochemistry, 43(14):4128-4136).

Accordingly, one embodiment of the invention relates to a genetically modified host cell or microorganism, wherein the host cell or microorganism has been genetically modified to express a core PUFA synthase system as described herein, and also a PPTase as described herein. Suitable PPTases are described above and are also described in the art. The PPTase may be expressed on the same or a different construct as one or more of the nucleic acid molecules encoding the core PUFA synthase protein or proteins. In one aspect, the PPTase is the *Nostoc* HetI.

Acyl-CoA Synthetases

Acyl-CoA synthetase (ACS) proteins catalyze the conversion of free fatty acids (FFAs), including long chain PUFA, to acyl-CoA. Numerous examples of polypeptides having ACS activity are known in the art and may be used in embodiments herein. For example, *Schizochytrium* sp. ATCC 20888 possesses one or more ACSs that are capable of converting the free fatty acid products of its PUFA synthase into acyl-CoA. See, e.g., U.S. Pat. No. 7,759,548.

The ACS protein can be derived from an organism that endogenously expresses a PUFA synthase system. Such organisms include, but are not limited to, a Thraustochytrid. In one aspect, the isolated ACS is derived from organisms of the genera *Schizochytrium, Thraustochytrium,* or *Ulkenia*. In another aspect, the isolated ACS is derived from *Schizochytrium* ATCC 20888. In another aspect, any ACS that functions in conjunction with any PUFA synthase system to increase the production and/or accumulation of PUFAs in a host cell or organism can be used in the present invention.

Genetically Modified Cells and Organisms

To produce significantly high yields of one or more desired polyunsaturated fatty acids or other bioactive molecules, an organism, preferably a microorganism, can be genetically modified to alter the activity and particularly, the end product(s), of the PUFA synthase system in the microorganism, or to introduce a PUFA synthase system into the microorganism. The present invention relates to methods to improve or enhance the effectiveness of such genetic modification and particularly, to improve or enhance the production and/or accumulation of the end product of a PUFA synthase system, preferably PUFA(s).

Therefore, one embodiment of the present invention relates to a genetically modified organism, wherein the organism expresses a PUFA synthase system, and wherein the organism has been genetically modified to express the enhancing factor protein(s) as described herein for the improvement of the production and/or accumulation of PUFAs (or other bioactive products of the PUFA synthase system) by the host. If the PUFA synthase system is heterologous to the host, then the organism is also preferably genetically modified to express a PPTase as a PUFA synthase accessory protein, which is described in detail above. In some embodiments, the organism has been genetically modified to express the one or more enhancing factor proteins described herein, and preferably a combination of TE2 and TE3 proteins or their homologues or enzymatically active fragments.

In one embodiment, if the PUFA synthase system is endogenous to the host, the organism can be genetically modified to express heterologous enhancing factor protein(s) as described above which improves the production and/or accumulation of PUFAs (or another bioactive product of the PUFA synthase system) in the host organism.

In another embodiment, the host organisms can be genetically modified to express a heterologous PUFA synthase system. The PUFA synthase system expressed by the organism can include any PUFA synthase system, for example, PUFA PKS systems that are entirely derived from a *Schizochytrium* 20888 PUFA synthase system, as well as PUFA synthase systems that are produced by "mixing and matching" nucleic acid sequences encoding proteins and/or domains from different PUFA synthase systems (e.g., by mixing *Schizochytrium* 20888 PUFA synthase proteins and/or domains with PUFA synthase proteins and/or domains from, e.g., *Schizochytrium* 9695, or those derived from the genera *Thraustochytrium, Ulkenia, Shewanella, Moritella*, and/or *Photobacterium*, etc.) and/or from different non-PUFA synthase systems (e.g., type I modular, type I iterative, type II or type III PKS systems), where the proteins and/or domains from different organisms are combined to form a complete, functional PUFA synthase system. PUFA synthase systems, including combining PUFA synthase genes or proteins from different organisms, are described in detail in U.S. Pat. Nos. 6,140,486; 6,566,583; Metz et al., *Science* 293:290-293 (2001); U.S. Pat. Nos. 7,247,461; 7,211,418; 7,217,856, U.S. Patent Application Publication No. 2010-0266564; and PCT Publication No. WO 2006/135866; supra). PUFA synthase genes and proteins are also disclosed in: U.S. Pat. Nos. 7,939,305; and 7,208,590. Each of the above-identified disclosures, and the genes and proteins described therein, is incorporated herein by reference.

Accordingly, encompassed by the present invention are methods to genetically modify organisms by: expressing one or more exogenous enhancing factor proteins described herein, especially a combination of enhancing factor proteins TE2 and TE3, and/or by genetically modifying at least one nucleic acid sequence in the organism that encodes at least one functional domain or protein (or biologically active fragment or homologue thereof) of a PUFA synthase system, including, but not limited to, any PUFA synthase system specifically described herein. In one embodiment, any of the exogenously introduced nucleic acid sequences can be optimized for codon usage or improved expression in the host. In one embodiment, any of the introduced nucleic acid sequences can be targeted to one or more organelles in the organism. Various embodiments of such sequences, methods to genetically modify an organism, specific modifications, and combinations thereof have been described in detail above and are encompassed here. Typically, the method is used to produce a particular genetically modified organism that produces a particular bioactive molecule or molecules.

Preferred genetically modified organisms include genetically modified microorganisms.

Preferably, a genetically modified organism of the invention produces one or more polyunsaturated fatty acids including, but not limited to, DHA (C22:6, n-3), DPA (C22:5, n-6 or n-3), EPA (C20:5, n-3), ARA (C20:4, n-6), GLA (C18:3, n-6), ALA (C18:3, n-3), and/or SDA (C18:4, n-3)), and more preferably, one or more longer chain PUFAs, including, but not limited to, DHA (C22:6, n-3), DPA (C22:5, n-6 or n-3), EPA (C20:5, n-3), or DTA (C22:4, n-6), or any combination thereof. In a particularly preferred embodiment, a genetically modified microorganism of the invention produces one or more polyunsaturated fatty acids including, but not limited to, DHA (C22:6, n-3) and DPA (C22:5, n-6 or n-3), or any combination thereof.

According to the present invention, a genetically modified organism includes an organism that has been modified using recombinant technology or by classical mutagenesis and screening techniques. As used herein, genetic modifications that result in a decrease in gene expression, in the function of the gene, or in the function of the gene product (i.e., the protein encoded by the gene) can be referred to as inactivation (complete or partial), deletion, interruption, blockage or down-regulation of a gene. For example, a genetic modification in a gene which results in a decrease in the function of the protein encoded by such gene, can be the result of a complete deletion of the gene (i.e., the gene does not exist, and therefore the protein does not exist), a mutation in the gene which results in incomplete or no translation of the protein (e.g., the protein is not expressed), or a mutation in the gene which decreases or abolishes the natural function of the protein (e.g., a protein is expressed which has decreased or no enzymatic activity or action). Genetic modifications that result in an increase in gene expression or function can be referred to as amplification, overproduction, overexpression, activation, enhancement, addition, or up-regulation of a gene.

Genetically Modified Microorganisms

As used herein, a genetically modified microorganism can include a genetically modified bacterium, protist, microalgae, algae, fungus, or other microbe. Such a genetically modified microorganism has a genome which is modified (i.e., mutated or changed) from its normal (i.e., wild-type or naturally occurring) form such that the desired result is achieved (i.e., increased or modified PUFA synthase activity and/or production and accumulation of a desired product using the PUFA PKS system). Genetic modification of a microorganism can be accomplished using classical strain development and/or molecular genetic techniques. Such techniques known in the art and are generally disclosed for microorganisms, for example, in Sambrook et al., 1989, *Molecular Cloning: A Laboratory Manual*, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

Examples of suitable host microorganisms for genetic modification include, but are not limited to, yeast including *Saccharomyces cerevisiae, Saccharomyces carlsbergensis*, or other yeast such as *Candida, Kluyveromyces*, or other fungi, for example, filamentous fungi such as *Aspergillus, Neurospora, Penicillium*, etc. Bacterial cells also may be used as hosts. These include, but are not limited to, *Escherichia coli*, which can be useful in fermentation processes. Alternatively, and only by way of example, a host such as a *Lactobacillus* species or *Bacillus* species can be used as a host.

Other hosts for use in the present invention include microorganisms from a genus including, but not limited to: *Thraustochytrium, Japonochytrium, Aplanochytrium, Elina* and *Schizochytrium* within the Thraustochytriaceae, and *Labyrinthula, Labyrinthuloides*, and *Labyrinthomyxa* within the Labyrinthulaceae. Preferred species within these genera include, but are not limited to: any species described below. Particularly preferred strains of Thraustochytriales include, but are not limited to: *Schizochytrium* sp. (S31)(ATCC 20888); *Schizochytrium* sp. (ATCC PTA-9695): *Schizochytrium* sp. (S8)(ATCC 20889); *Schizochytrium* sp. (LC-RM) (ATCC 18915); *Schizochytrium* sp. (SR21); *Schizochytrium* sp. N230D, *Schizochytrium aggregatum* (Goldstein et Belsky) (ATCC 28209); *Schizochytrium limacinum* (Honda et Yokochi) (IFO 32693); *Thraustochytrium* sp. (23B)(ATCC 20891 or ATCC 20892); *Thraustochytrium striatum* (Schneider)(ATCC 24473); *Thraustochytrium aureum* (Goldstein) (ATCC 34304); *Thraustochytrium roseum* (Goldstein) (ATCC 28210); and *Japonochytrium* sp. (L1) (ATCC 28207).

In one embodiment of the present invention, the enhancing factor proteins of PUFA synthase (e.g., TE2 and TE3) of a microorganism are exogenously introduced into a host microorganism which has an endogenous PUFA synthase system to increase the amount of PUFAs produced. In another embodiment, the exogenous enhancing factor proteins and an exogenous PUFA synthase system of a microorganism are introduced into a host microorganism which does not have any PUFA synthase system to produce detectable amount of PUFAs. Examples of heterologous sequences that could be introduced into a host genome include sequences encoding at least one functional PUFA synthase domain or protein from another PKS synthase or even an entire PUFA synthase system (e.g., all genes associated with the PUFA synthase system). A heterologous sequence can also include a sequence encoding a modified functional domain (a homologue) of a natural domain from a PUFA synthase system. Other heterologous sequences that can be introduced into the host genome include PPTase and/or ACS.

Therefore, it is an object of the present invention to produce, via the genetic manipulation of microorganisms as described herein, PUFAs and, by extension, oils obtained from such microorganisms comprising these PUFAs. Examples of PUFAs that can be produced by the present invention include, but are not limited to, DHA (docosahexaenoic acid (C22:6, n-3)), DPA (docosapentaenoic acid (C22:5, n-6 or n-3)), and EPA (eicosapentaenoic acid (C20:5, n-3)) and any combinations thereof. The present invention allows for the production of commercially valuable lipids enriched in one or more desired (primary) PUFAs by the present inventors' development of genetically modified microorganisms through the use of the PUFA synthase system that produces PUFAs.

When using a PUFA synthase system as preferred in the present invention, a given PUFA synthase system derived from a particular organism will produce particular PUFA(s), such that selection of a PUFA synthase system from a particular organism will result in the production of specified PUFAs. For example, use of a PUFA synthase system from *Schizochytrium* 20888 will result in the production of DHA and DPAn-6 as the primary PUFAs.

*Schizochytrium* 20888 can accumulate high levels of oil (>60% of the biomass) and DHA can comprise>40% of the fatty acids present in that biomass. In the native organism the DHA to DPAn-6 ratio typically ranges between 2.3 to 2.7. Expression of the PUFA synthase subunits of *Schizochytrium* 20888, along with an appropriate PPTase (e.g., HetI from *Nostoc* sp.) in heterologous host cells has resulted in production of DHA and DPAn-6 in those cells. Although DHA and DPAn-6 are produced in cells of *E. coli*, and in yeast and higher plants, the levels have not approached those observed in the native organism. Additionally, in both yeast and in plants, the DHA to DPAn-6 ratio is typically significantly lower than that observed in the native organism.

According to the present invention, a microorganism can be genetically modified to introduce one or more genes encoding the enhancing factor proteins described herein to increase the production of PUFAs from the particular PUFA synthase present in that organism (e.g., DHA, DPAn-6 and/or EPA). In addition, introduction of the enhancing factor proteins described herein can result in an alteration of the relative amounts of the PUFAs produced by the particular PUFA synthase present in that organism (e.g., the ratio of DHA to DPAn-6 produced in the microorganism may be increased).

Therefore, one embodiment of the present invention relates to a genetically modified microorganism (e.g., wherein the microorganism has been genetically modified to express a PUFA synthase system described herein), which includes the core PUFA synthase, a PPTase, and/or an ACS, as described herein, wherein the microorganism has been further genetically modified to express one or more enhancing factor proteins as described herein for the improvement of the production and/or accumulation of PUFAs (or other bioactive products of the PUFA synthase system) by the host. Preferably, such enhancing factor protein is a combination of TE2 and TE3 proteins. The enhancing factor proteins described here, such as TE2 and TE3, include homologues and biologically active fragments of such proteins.

In some embodiments, the genetically modified microorganism which is genetically modified to express a heterologous PUFA synthase system and a combination of TE2 and TE3 proteins has an increased level of total PUFA accumulation relative to the microorganism without the expression of TE2 and TE3 proteins. In one embodiment, the total PUFA accumulation is increased more than 2-fold, more than 3-fold, more than 4-fold, more than 5-fold, more than 6-fold, more than 7-fold, more than 8-fold, more than 9-fold, or more than 10-fold. In one embodiment, the increased level of total PUFA accumulation is close or equal to the level produced by the native microorganism of the heterologous PUFA synthase system. In one embodiment, the increased level of total PUFA accumulation is between 90% and 110% of the amount of PUFA produced by the native microorganism of the heterologous PUFA synthase system.

In some embodiments, the genetically modified microorganism which is genetically modified to express a heterologous PUFA synthase system and a combination of TE2 and TE3 proteins has an increased level of total DHA, DPA(n-6), and EPA accumulation when compared to the microorganism without the expression of TE2 and TE3 proteins. In one embodiment, the level of DHA and DPAn-6 accumulation is increased more than 2-fold, more than 3-fold, more than 4-fold, more than 5-fold, more than 6-fold, more than 7-fold, more than 8-fold, more than 9-fold, or more than 10-fold. In one embodiment, the increased level of DHA and DPAn-6 accumulation is close or equal to the level produced by the native microorganism of the heterologous PUFA synthase system. In one embodiment, the increased level of DHA and DPAn-6 accumulation is between 90% and 110% of the amount of PUFA produced by the native microorganism of the heterologous PUFA synthase system.

In some embodiments, the genetically modified microorganism which is genetically modified to express a heterologous PUFA synthase system and a combination of TE2 and TE3 proteins has an enhanced ratio of DHA:DPAn-6 by weight of total fatty acids than the microorganism without such genetic modification. In one embodiment, the higher ratio of DHA:DPAn-6 is close or equal to the ratio in the microorganism where the PUFA synthase system is derived from. In one embodiment, the enhanced ratio of DHA:DPAn-6 is between 90% and 110% of the ratio of DHA:DPAn-6 of the microorganism where the PUFA synthase system is derived from.

The genetic modification of a microorganism according to the present invention can be made either to positively affect the activity of the PUFA synthase system expressed by the microorganism, or to negatively affect the activity of the PUFA synthase system expressed by the microorganism. For example, the activity of the PUFA synthase system can be reduced or even blocked by a reduction or elimination of the expression of the endogenous enhancing factor proteins of the host microorganism. In some embodiments, the host microorganism is a Thraustochytriales microorganism. In one embodiment, the host microorganism is a *Schizochytrium* 20888. In another embodiment, the host microorganism is a *Schizochytrium* 9695.

Uses for Genetically Modified Organisms of the Invention

One embodiment of the present invention is a method to produce desired bioactive molecules (also referred to as products or compounds) by growing a genetically modified microorganism of the present invention (described in detail above). Preferably, the bioactive molecule is a PUFA, and most preferably, an LCPUFA. Preferably, the genetically modified microorganism is a genetically modified microorganism. Such a method includes, for example, the step of culturing in a fermentation medium a microorganism as described previously herein and in accordance with the present invention. Preferred host cells and microorganisms for genetic modification related to the PUFA synthase system of the invention are described above.

One embodiment of the present invention is a method to produce desired PUFAs by culturing a genetically modified microorganism of the present invention (described in detail above). Such a method includes the step of culturing in a fermentation medium and under conditions effective to produce the PUFA(s) a microorganism that has a genetic modification as described previously herein and in accordance with the present invention. An appropriate, or effective, medium refers to any medium in which a genetically modified microorganism of the present invention, when cultured, is capable of producing the desired PUFA product(s). Such a medium is typically an aqueous medium comprising assimilable carbon, nitrogen and phosphate sources. Such a medium can also include appropriate salts, minerals, metals and other nutrients. Any microorganisms of the present invention can be cultured in conventional fermentation bioreactors. The microorganisms can be cultured by any fermentation process which includes, but is not limited to, batch, fed-batch, cell recycle, and continuous fermentation. Preferred growth conditions for Thraustochytrid microorganisms according to the present invention are well known in the art and are described in detail, for example, in U.S. Pat. Nos. 5,130,242, 5,340,742, and 5,698,244, each of which is incorporated herein by reference in its entirety.

The desired PUFA(s) and/or other bioactive molecules produced by the genetically modified microorganism can be recovered from the fermentation medium using conventional separation and purification techniques. For example, the fermentation medium can be filtered or centrifuged to remove microorganisms, cell debris and other particulate matter, and the product can be recovered from the cell-free supernatant by conventional methods, such as, for example, ion exchange, chromatography, extraction, solvent extraction, phase separation, membrane separation, electrodialysis, reverse osmosis, distillation, chemical derivatization and crystallization. Alternatively, microorganisms producing the PUFA(s), or extracts and various fractions thereof, can be used without removal of the microorganism components from the product.

The invention further includes any microorganisms described herein as well as any oils produced by the microorganisms described herein. The invention also includes any products produced using the microorganisms or oils described herein.

One embodiment of the present invention relates to a method to modify a product containing at least one fatty acid, comprising adding to the product a microorganism or oil produced by a genetically modified microorganism according to the invention and as described herein (e.g., a microorganism that has been genetically modified with a PUFA synthase system, makes use of any of the strategies for improvement of production and/or accumulation of PUFAs described herein, and has a fatty acid profile described herein). Any products produced by this method or generally containing any microorganisms or oils from the microorganisms described herein are also encompassed by the invention.

Preferably, the product is selected from the group consisting of a food, a dietary supplement, a pharmaceutical formulation, a feedstuff, a humanized animal milk, and an infant formula. Suitable pharmaceutical formulations include, but are not limited to, an anti-inflammatory formulation, a chemotherapeutic agent, an active excipient, an osteoporosis drug, an anti-depressant, an anti-convulsant, an anti-*Heliobactor pylori* drug, a drug for treatment of neurodegenerative disease, a drug for treatment of degenerative liver disease, an antibiotic, and a cholesterol lowering formulation. In one embodiment, the product is used to treat a condition selected from the group consisting of: chronic inflammation, acute inflammation, gastrointestinal disorder, cancer, cachexia, cardiac restenosis, neurodegenerative disorder, degenerative disorder of the liver, blood lipid disorder, osteoporosis, osteoarthritis, autoimmune disease, preeclampsia, preterm birth, age related maculopathy, pulmonary disorder, and peroxisomal disorder.

In some embodiments of the invention, the PUFAs produced by the genetically modified organisms or the methods disclosed in the present invention can be incorporated into a component of food or feed (e.g., a food supplement). Types of food products into which the PUFAs can be incorporated according to the present invention are not particularly limited, and include food products such as fine bakery wares, bread and rolls, breakfast cereals, processed and unprocessed cheese, condiments (ketchup, mayonnaise, etc.), dairy products (milk, yogurt), puddings and gelatine desserts, carbonated drinks, teas, powdered beverage mixes, processed fish products, fruit-based drinks, chewing gum, hard confectionery, frozen dairy products, processed meat products, nut and nut-based spreads, pasta, processed poultry products, gravies and sauces, potato chips and other chips or crisps, chocolate and other confectionery, soups and soup mixes, soya based products (milks, drinks, creams, whiteners), vegetable oil-based spreads, and vegetable-based drinks.

Examples of feedstuffs into which the PUFAs produced in accordance with the present invention may be incorporated include, for instance, pet foods such as cat foods, dog foods and the like, feeds for aquarium fish, cultured fish or crustaceans, etc., feed for farm-raised animals (including livestock and further including fish or crustaceans raised in aquaculture). The PUFA containing genetically modified organisms produced in accordance with the present invention, such as the genetically modified microorganisms, may be incorporated directly into feed products.

General Definitions and Guidance

According to the present invention, an "isolated" protein or nucleic acid is a protein or nucleic acid that has been substantially separated, produced apart from or purified away from other biological components in the cell of the organism in which the protein or the nucleic acids naturally occurs. "Isolated" effects a chemical or functional change in the protein or nucleic acid (e.g., a nucleic acid may be isolated from a chromosome by breaking chemical bonds connecting the nucleic acid to the remaining DNA in the chromosome). Nucleic acid molecules and proteins that have been "isolated" include nucleic acid molecules and proteins purified by standard purification methods. "Isolated" does not reflect the extent to which the protein or nucleic acid has been purified. The term also embraces nucleic acids and proteins prepared by recombinant expression in a host cell, as well as chemically-synthesized nucleic acid molecules, proteins, and peptides. As used herein, the term "nucleic acid molecule" may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide." A nucleic acid molecule is usually at least 10 bases in length, unless otherwise specified. The term includes single- and double-stranded forms of DNA. A nucleic acid molecule can include either or both naturally occurring and modified nucleotides linked together by naturally occurring and/or non-naturally occurring nucleotide linkages.

According to the present invention, a "recombinant" nucleic acid is a nucleic acid that is constructed by joining two or more nucleic acid molecules and that can replicate in a living cell. One embodiment of the present invention includes a recombinant nucleic acid molecule comprising a recombinant vector and a nucleic acid sequence described above. Such nucleic acid sequence encodes a protein or peptide having a biological activity of any of the EF-X proteins described above. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

In one embodiment, a recombinant vector used in a recombinant nucleic acid molecule of the present invention is an expression vector. As used herein, the phrase "expression vector" is used to refer to a vector that is suitable for production of an encoded product (e.g., a protein of interest). In this embodiment, a nucleic acid sequence encoding the product to be produced (e.g., a PUFA PKS domain or protein) is inserted into the recombinant vector to produce a recombinant nucleic acid molecule. The nucleic acid sequence encoding the protein to be produced is inserted into the vector in a manner that operatively links the nucleic acid sequence to regulatory sequences in the vector that enable the transcription and translation of the nucleic acid sequence within the recombinant host cell.

In another embodiment, a recombinant vector used in a recombinant nucleic acid molecule of the present invention is a targeting vector. As used herein, the phrase "targeting vector" is used to refer to a vector that is used to deliver a particular nucleic acid molecule into a recombinant host cell, wherein the nucleic acid molecule is used to delete, inactivate, or replace an endogenous gene or portion of a gene within the host cell or microorganism (i.e., used for targeted gene disruption or knock-out technology). Such a vector may also be known in the art as a "knock-out" vector. In one aspect of this embodiment, a portion of the vector, but more typically, the nucleic acid molecule inserted into the vector (i.e., the insert), has a nucleic acid sequence that is homologous to a nucleic acid sequence of a target gene in the host cell (i.e., a gene which is targeted to be deleted or inactivated). The nucleic acid sequence of the vector insert is designed to associate with the target gene such that the target gene and the insert may undergo homologous recombination, whereby the endogenous target gene is deleted, inactivated, attenuated (i.e., by at least a portion of the endogenous target gene being mutated or deleted), or replaced. The use of this type of recombinant vector to replace an endogenous *Schizochytrium* gene, for example, with a recombinant gene has been previously described by the present inventors, and the general technique for genetic transformation of Thraustochytrids is described in detail in U.S. Pat. No. 7,001,772.

As used herein, the term "lipid" includes phospholipids; free fatty acids; esters of fatty acids; triacylglycerols; diacylglycerides; monoacylglycerides; lysophospholipids; soaps; phosphatides; waxes (esters of alcohols and fatty acids); sterols and sterol esters; carotenoids; xanthophylls (e.g., oxycarotenoids); hydrocarbons; and other lipids known to one of ordinary skill in the art.

Reference to a particular protein from a specific organism or to a particular protein being derived from a specific organism, such as a "TE2 derived from *Schizochytrium* sp. ATCC-20888" or "Sz-TE2", by way of example, refers to a TE2 (including a homologue of the naturally occurring TE2) from a *Schizochytrium* sp. ATCC-20888 or a Sz-TE2 that has been otherwise produced from the knowledge of the structure (e.g., sequence) of a naturally occurring TE2 from *Schizochytrium*. In other words, a Sz-TE2 includes any TE2 that has the structure and function of a naturally occurring TE2 from *Schizochytrium* or that has a structure and function that is sufficiently similar to a TE2 from *Schizochytrium* such that the TE2 is a biologically active (i.e., has biological activity) homologue of a naturally occurring TE2 from *Schizochytrium* sp. As such, a Sz-TE2 can include purified, partially purified, recombinant, mutated/modified and synthetic proteins.

According to the present invention, the terms "modification" and "mutation" can be used interchangeably, particularly with regard to the modifications/mutations to the primary amino acid sequences of a protein or peptide (or nucleic acid sequences) described herein. The term "modification" can also be used to describe post-translational modifications to a protein or peptide including, but not limited to, methylation, farnesylation, carboxymethylation, geranyl geranylation, glycosylation, phosphorylation, acetylation, myristoylation, prenylation, palmitation, and/or amidation. Modifications can also include, for example, complexing a protein or peptide with another compound. Such modifications can be considered to be mutations, for example, if the modification is different than the post-translational modification that occurs in the natural, wild-type protein or peptide.

As used herein, the term "homologue" is used to refer to a protein or peptide which differs from a naturally occurring protein or peptide (i.e., the "prototype" or "wild-type" protein) by one or more minor modifications or mutations to the naturally occurring protein or peptide, but which maintains the overall basic protein and side chain structure of the naturally occurring form (i.e., such that the homologue is identifiable as being related to the wild-type protein). Such changes include, but are not limited to: changes in one or a few (e.g., 1% or less) amino acid side chains; changes in one or a few (e.g., 1% or less) amino acids, including deletions (e.g., a truncated version of the protein or peptide) insertions and/or substitutions; changes in stereochemistry of one or a few (e.g., 1% or less) atoms; and/or minor derivatizations, including but not limited to: methylation, farnesylation, geranyl geranylation, glycosylation, carboxymethylation, phosphorylation, acetylation, myristoylation, prenylation, palmitation, and/or amidation. A homologue can have either enhanced, decreased, or substantially similar properties as compared to the naturally occurring protein or peptide. Preferred homologues of a protein are described in detail below. It is noted that homologues can include synthetically produced homologues, naturally occurring allelic variants of a given protein or domain thereof, or homologous sequences from organisms other than the organism from which the reference sequence was derived.

Conservative substitutions typically include substitutions within the following groups: glycine and alanine; valine, isoleucine and leucine; aspartic acid, glutamic acid, asparagine, and glutamine; serine and threonine; lysine and arginine; and phenylalanine and tyrosine. Substitutions may also be made on the basis of conserved hydrophobicity or hydrophilicity (Kyte and Doolittle, *J. Mol. Biol.* 157:105 (1982)), or on the basis of the ability to assume similar polypeptide secondary structure (Chou and Fasman, *Adv. Enzymol.* 47: 45 (1978)).

Homologues can be the result of natural allelic variation or natural mutation. A naturally occurring allelic variant of a nucleic acid encoding a protein is a gene that occurs at essentially the same locus (or loci) in the genome as the gene which encodes such protein, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

Modifications or mutations in protein homologues, as compared to the wild-type protein, either increase, decrease, or do not substantially change, the basic biological activity of the homologue as compared to the naturally occurring (wild-type) protein. In general, the biological activity or biological action of a protein refers to any function(s) exhibited or performed by the protein that is ascribed to the naturally occurring form of the protein as measured or observed in vivo (i.e., in the natural physiological environment of the protein) or in vitro (i.e., under laboratory conditions). Biological activities of PUFA PKS systems and the individual proteins/domains that make up a PUFA synthase system have been described in detail elsewhere herein and in the referenced patents and applications.

Modifications of a protein, such as in a homologue, may result in proteins having the same biological activity as the naturally occurring protein, or in proteins having decreased or increased biological activity as compared to the naturally occurring protein. Modifications which result in a decrease in protein expression or a decrease in the activity of the protein, can be referred to as inactivation (complete or partial), down-regulation, or decreased action (or activity) of a protein. Similarly, modifications which result in an increase in protein expression or an increase in the activity of the protein, can be referred to as amplification, overproduction, activation, enhancement, up-regulation or increased action (or activity) of a protein. It is noted that general reference to a homologue having the biological activity of the wild-type protein does not necessarily mean that the homologue has identical biological activity as the wild-type protein, particularly with regard to the level of biological activity. Rather, a homologue can perform the same biological activity as the wild-type protein, but at a reduced or increased level of activity as compared to the wild-type protein. A functional domain of a protein is a domain (i.e., a domain can be a portion of a protein) that is capable of performing a biological function (i.e., has biological activity).

As used herein, the term "biologically active fragment" refers to a portion of a protein which such fragment maintains at least part of the biological activity of the protein. For example, the biological active fragment of TE2 is a portion of TE2 and it maintains at least part of the biological activity of TE2 which enhances the enzymatic activity of PUFA synthase in the host cell where TE2 is exogenously expressed.

The term "PUFA synthase" as used herein refers to an enzyme that produces PUFAs (e.g., LCPUFAs), as well as a domain of such an enzyme. Some specific PUFA synthases are designated herein by an additional notation (e.g., "*Schizochytrium* 20888 PUFA synthase"). The term "PUFA synthase system" refers to one or more PUFA synthase(s) and any accessory enzyme that can affect the function of the PUFA synthase (e.g., a PPTase). For example, the PUFA synthase system in *Schizochytrium* 20888 consists of the native PUFA synthase subunits and the native PPTase.

As used herein, the term "transformation" or "transduction" refers to the transfer of one or more nucleic acid molecule(s) into a cell. A cell is "transformed" by a nucleic acid molecule transduced into the cell when the nucleic acid molecule becomes stably replicated by the cell, either by incorporation of the nucleic acid molecule into the cellular genome, or by episomal replication. As used herein, the term "transformation" encompasses all techniques by which a nucleic acid molecule can be introduced into such a cell.

The term "sequence identity" or "identity," as used herein in the context of two nucleic acid or polypeptide sequences, may refer to the residues in the two sequences that are the same when aligned for maximum correspondence over a specified comparison window. As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) Adv. Appl. Math. 2:482; Needleman and Wunsch (1970) J. Mol. Biol. 48:443; Pearson and Lipman (1988) Proc. Natl. Acad. Sci. U.S.A. 85:2444; Higgins and Sharp (1988) Gene 73:237-44; Higgins and Sharp (1989) CABIOS 5:151-3; Corpet et al. (1988) Nucleic Acids Res. 16:10881-90; Huang et al. (1992) Comp. Appl. Biosci. 8:155-65; Pearson et al. (1994) Methods Mol. Biol. 24:307-31; Tatiana et al. (1999) FEMS Microbiol. Lett. 174:247-50. A detailed consideration of sequence alignment methods and homology calculations can be found in, e.g., Altschul et al. (1990) J. Mol. Biol. 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Align two or more sequences" function of the BLAST™ (blastn) program may be employed using the default parameters. For comparisons of protein sequences, the "Align two or more sequences" function of the BLAST™ (blastp) program may be employed using the default parameters. As used herein, hybridization conditions refer to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press (1989). Sambrook et al., ibid., is incorporated by reference herein in its entirety (see specifically, pages 9.31-9.62). In addition, formulae to calculate the appropriate hybridization and wash conditions to achieve hybridization permitting varying degrees of mismatch of nucleotides are disclosed, for example, in Meinkoth et al., *Anal. Biochem.* 138, 267 (1984); Meinkoth et al., ibid., incorporated by reference herein in its entirety.

More particularly, moderate stringency hybridization and washing conditions, as referred to herein, refer to conditions which permit isolation of nucleic acid molecules having at least about 70% nucleic acid sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleic acid sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleic acid sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. In particular embodiments, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. In particular embodiments, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature for molecules larger than about 100 nucleotides, 0% formamide and a G+C content of about 40%. Alternatively, $T_m$ can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated $T_m$ of a particular hybrid, and wash conditions typically include a combination of salt and temperature conditions that are approximately 12-20° C. below the calculated $T_m$ of the particular hybrid. One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Each publication, patent or patent application referenced herein is incorporated herein by reference in its entirety.

The following examples are provided for the purpose of illustration and are not intended to limit the scope of the present invention.

EXAMPLES

Example 1

The following example describes the development of an assay used to identify factors which may enhance the enzymatic activity of PUFA synthases.

This in vitro assay was developed to identify any factors present in homogenates of cells of Schizochytrium 20888, which could facilitate the activity of a PUFA synthase system. The assay was based on an observation that addition of an extract derived from a strain of Schizochytrium 20888 to a homogenate of E. coli expressing the Schizochytrium 20888 PUFA synthase (plus HetI) resulted in an increase in the in vitro activity of that PUFA synthase system (see the left two samples of FIG. 2, i.e., BUFF K and Q-KO). The general features of this assay are described below.

Preparation of homogenates of an E. coli strain expressing the Schizochytrium 20888 PUFA synthase for use in the PUFA synthase enhancement assay: the Schizochytrium 20888 PUFA synthase subunits and HetI (from Nostoc sp.) were expressed in E. coli strain JK824 as described in Hauvermale et al., 2008, Lipids, 41:739-747 and Metz et al., US Patent Application Publication No. 2013-0150599. The PUFA synthase subunit genes were expressed as a synthetic operon under control of the T7 promoter system while HetI was expressed constitutively on a separate plasmid. For biochemical assays, strain JK824 was typically grown in Luria Broth supplemented with 10% glycerol at 30° C. to an O.D. (600 nm) of ~1 and then Isopropyl β-D-1-thiogalactopyranoside (IPTG) was added (to a final concentration of 1 mM) to induce the production of the T7 polymerase. Approximately 4 hrs after induction, the cells were harvested, washed and resuspended in Buffer KE (Buffer K—50 mM NaPO$_4$, pH 6.8 with 10% glycerol—which also contained 1 mM EDTA and 2 mM dithioerytheitol). The cells were ruptured by passage through a French Pressure Cell (16,000 psi) and the homogenate separated into aliquots and stored at −80° C. for use in the PUFA synthase activity enhancement assay.

In vitro PUFA synthase activity enhancement assays: The in vitro PUFA synthase assay involves measurement of radioactivity, from $^{14}C$ labeled malonyl-CoA, incorporated into DHA and DPAn-6. The general characteristics of a PUFA synthase assay are described in Metz et al., 2009, Plant Physiology and Biochemistry 47:472-478. The typical enhancement assay had a final volume of 100 μL—consisting of 40 μL of the homogenate derived from E. coli strain JK824 (described above), 40 uL of a sample to be evaluated (e.g., homogenates of Schizochytrium strains, or chromatographic fractions) and 10 μL of reaction cocktail (containing a mixture of cold and [2-$^{14}C$]-malonyl-CoA and NADPH). The JK824 homogenate and the sample to be evaluated were mixed just prior to addition of the reaction cocktail. The components of the reaction cocktail were adjusted so that the final concentrations of malonyl-CoA and NADPH in the assay were 50 μM and 2 mM, respectively. Buffer K served as the negative control for the enhancement of activity and was also used to adjust the volume of the samples being evaluated to 40 μL when less than that amount was being tested. The assay reactions were carried out in glass tubes in a room temperature (~21° C.) water bath. The time of incubation was dependent on the experimental requirements.

The in vitro assay products of the Schizochytrium 20888 PUFA synthase are free fatty acids (Metz et al., 2009, Plant Physiology and Biochemistry 47:472-478). The incorporation of radioactivity into these free fatty acids was routinely measured by extraction with organic solvents and lipid class separation on TLC plates. Occasionally the extracted lipids were converted to FAMEs prior to separation on TLC plates to confirm that DHA and DPAn-6 were the primary fatty acids being labeled in the assay. The in vitro assay reactions were stopped by one of two methods depending on the work-up protocol. For conversion of fatty acids to fatty acid methyl-esters (FAMEs) using an acidic method, the reaction was stopped by adding the FAME reagent (see below). For extraction of lipids without derivatization, the reaction was stopped by addition of 125 μL of isopropanol:acetic acid (4:1 v/v) (see below).

Acidic FAME Protocol:

the reaction was stopped by adding 2.0 mL of 4% HCl in methanol plus 50 μL toluene, the glass tubes were sealed with Teflon lined caps and heated at 100° C. for 1 hr. The reaction was cooled to room temperature, then 1.0 mL of hexane and 0.5 mL water was added, further vortexed then left to separate. If desired, a portion can be removed for liquid scintillation counting (LSC). An aliquot of ~600 μL of organic phase was transferred to a new tube and the solvent was removed under N$_2$. The residue was dissolve in 50 μL hexane and spotted onto either Silica gel 60 A TLC plates (develop with hexane:diethyl-ether:acetic acid—70:30:2) or Silica Gel G plates soaked in 10% AgNO$_3$/90% acetonitrile (activated for 30 min at 100° C. prior to use) (developed w/hexane:diethyl-ether/acetic acid—70:20:2). The plates were left to air dry and radioactive areas were detected using phosphorimaging technology.

HIP Protocol—Extraction of Underivatized Lipids:

As indicated above, the reaction was stopped by adding 125 μL of isopropanol:acetic acid (4:1 v/v) then adding 2 mL of hexane:isopropanol (3:2, v/v), further vortexed then 1 mL of 6.7% (w/v) sodium sulfate was added and vortexed again. The phases were left to separate. If desired, a portion of the organic (upper) phase was transferred for LSC then the rest (~1.0 mL) was transferred to a new tube. The solvent was remove with N$_2$ gas and the residue was dissolved in 50 μL of hexane. The sample was spotted on a silica gel 60 A TLC plate and developed with hexane:diethyl-ether:acetic acid (70:30:2). The plates were let air dry and radioactive areas were detected using phosphorimaging technology.

Assay for identifying PUFA synthase enhancing factor proteins: for the PUFA synthase enhancement assay, extracts derived from one of several *Schizochytrium* strains were combined with the above mentioned *E. coli* extract prior to addition of the $^{14}$C labeled malonyl-CoA and NADPH. Reactions in which the extraction buffer solution was combined with the *E. coli* material instead of the cell extracts served as negative controls. Several strains were used for these experiments.

Example 2

The following example describes the strains, derived from *Schizochytrium* 20888, that were utilized to develop the in vitro PUFA synthase enhancement assay and to identify the enhancing factors.

Quad K-O: Quad-KO is a *Schizochytrium* 20888 strain in which the three PUFA synthase subunit open reading frames (Orfs) and the FAS Orf were deleted and replaced with antibiotic resistance gene cassettes. This strain was created using the methods described in Hauvermale et al., 2008, Lipids, 41: 739-747, Metz et al., 2009, Plant Physiology and Biochemistry 47:472-478, and Roessler et al., 2006, U.S. Pat. No. 7,001,772. The Quad-KO strain requires supplementation of the media with both saturated and long chain polyunsaturated fatty acids for growth. Homogenates of this strain do not have the ability to incorporate radioactivity from $^{14}$C malonyl-CoA into fatty acids that are readily extracted by organic solvents. Extracts from this strain were used to establish the initial parameters for chromatographic enrichment of factors responsible for enhancement of PUFA synthase activity in the in vitro assays.

AC66: The cell wall of *Schizochytrium* 20888 is difficult to disrupt thus making preparation of cell-free homogenates challenging. AC66 is a strain of *Schizochytrium* 20888 that was selected after chemical mutagenesis based on colony morphology and was subsequently found to be easily disrupted by sonication. The fatty acid profile and oil accumulation properties of strain AC66 are very similar to those of its parent. The ease of cell disruption by sonication greatly simplifies preparation of cell-free homogenates for biochemical work.

AC66/DGAT KO: AC66/DGAT KO is a strain derived from AC66 in which a gene encoding a particular diacyl glycerol acyltransferase in *Schizochytrium* 20888 has been inactivated (described in Metz et al., 2013, US Patent Application Publication No. 2013-0150599, referred to in that patent as DAGAT-1). This strain, while prototrophic, does not accumulate significant amounts of oil. The lack of oil simplifies biochemical analysis and the initial steps of chromatographic enrichments of the PUFA synthase enhancing factors.

Example 3

The following example describes a procedure for chromatographic enrichment of the PUFA synthase in vitro activity enhancing factor(s) (EF-X) from extracts derived from strains of *Schizochytrium* 20888. It was determined subsequently by the experiments described in Example 4 that EF-X from extracts derived from strains of *Schizochytrium* 20888 actually contains two enhancing factors: Sz-TE2 and Sz-TE3.

Several chromatographic matrixes were tested for utility in enrichment of the EF-X. Initial testing was done using extracts from the Quad-KO strain since it lacks the FAS and PUFA synthase activities that could confound the enhancement assay. It was subsequently discovered that, by use of appropriate conditions, the EF-X activity present in cell free extracts of *Schizochytrium* 20888 could be cleanly separated from both the FAS and PUFA synthase activities by use of a Mimetic Blue A SA column. The starting material used for the example described below was derived from the AC66/DGAT-KO strain of *Schizochytrium* 20888.

Cell free homogenate preparation: Cells of the AC66/DGAT-KO strain were grown to mid-log phase, harvested by centrifugation, resuspended in 'Buffer K' (50 mM NaPO$_4$, pH 6.8 with 10% glycerol) and lysed by sonication. The homogenate was centrifuged (100,000×g×1 hr) and the supernatant collected and passed through a 0.2 µM filter to yield the starting material (S100F) used for chromatography.

Mimetic Blue SA chromatography: A Mimetic Blue SA matrix (Blue SA) was used for the initial chromatographic step. Approximately 50 mL of S100F was loaded onto a 10 mL column which had been equilibrated with Buffer K. The column was washed with Buffer K and then with Buffer K containing 0.24 M NaCl. Bound EF-X activity was eluted by a linear salt gradient (from 0.24 M to 2 M NaCl over 40 mL). Fractions (5 mL) were collected and assayed. Those with the highest EF-X activity (in the middle portion of the gradient) were pooled and taken to the next step.

Hydrophobic Interaction Chromatography (HIC): A portion (10 mL) of the pooled material from the Blue SA column was loaded directly on to a 1 mL HiTrap Phenyl-FF cartridge (GE HealthCare) which had been equilibrated with Buffer K containing 2 M NaCl. After washing with equilibration buffer, the bound EF-X activity was eluted using a 10 column volume reverse salt gradient (2 M to 0 M NaCl in Buffer K). Active fractions from multiple runs were pooled for the next step. The column was cleaned with 0.5 M NaOH between the runs.

Cation exchange chromatography: Pooled fractions from the HIC step were concentrated and desalted using ultrafiltration spin columns. A portion (2 mL) of the desalted material was loaded onto a 1 mL UNO-S cation exchange column (Bio-Rad) which had been equilibrated with Buffer K. After washing with Buffer K, the bound EF-X activity was eluted using a 10 column volume salt gradient (0 M to 1 M NaCl in Buffer K). Fractions (0.5 mL) were collected and EF-X activity assayed.

Size exclusion chromatography: Two fractions from the cation exchange column with the highest EF-X activity were combined then concentrated and desalted using ultrafiltration spin columns. A portion (500 µL) of this material was loaded on to a SuperDex 200 column (GE Health Care) which had been equilibrated with Buffer K. The EF-X activity was retained by the matrix and eluted as a single peak with an apparent molecular mass, estimated by comparison to protein standards of from 40 to 80 kDa. SDS-PAGE analysis (with silver staining of the gel) revealed only a few distinct polypeptide bands in the fractions with EF-X activity—and only three bands whose staining intensity appeared to correlate with the activity detected in those same fractions. The molecular masses of these proteins were estimated to be ~80 kDa, ~37 kDa and ~17 kDa, by comparison to protein standards separated on the same gel. Portions of the relevant fractions from the SuperDex 200 column were used for peptide generation and sequencing procedures. Peptide sequencing in conjunction with a *Schizochytrium* 20888 genome database was performed and EF-X candidates were identified.

Example 4

The following example describes the procedure utilized to identify two candidate proteins for association with the enhancement of in vitro PUFA synthase activity and the molecular characterization of those candidates.

LC-MSMS (liquid chromatography-tandem mass spectrometry) analysis was performed on tryptic peptides generated from fractions derived from the final chromatographic step (SuperDex 200 column separation) of Example 2. Candidate proteins for association with the *Schizochytrium* 20888 EF-X were identified. The method involves LC-MSMS sequencing (with a *Schizochytrium* 20888 genome sequence derived predicted protein database as a reference) in combination with correlation of relative peptide abundance determined by spectral counting of the LC-MSMS data with the EF-X activity assay results for each fraction. A list of 17 candidate proteins was generated. The top two candidates were identified as likely thioesterases by BLAST analysis. Both candidates showed homology to 4-hydroxybenzoyl-CoA-like thioesterases. The predicted nucleotide sequences and the deduced amino acid translations of the two candidate Orfs are provided in the 'Sequence Listing' and described below. The candidate proteins were termed Sz-TE2 and Sz-TE3. The Sz-TE2 protein is likely to be associated with the ~17 kDa band identified in the silver stained gel mentioned in the previous example while Sz-TE3 is likely to be associated with the ~37 kDa band. The third highest hit in the Spectral Counting list appeared to be correctly annotated in the genome database and showed very high homology to a bi-functional enzyme of the fatty acid degradation pathway. This protein is likely to be associated with the ~80 kDa identified in the silver stained gel. Follow up work was carried out with the Sz-TE2 and Sz-TE3 candidates. The molecular characteristics of the open reading frames and predicted encoded proteins are described here:

Sz-TE2: The nucleotide sequence of the predicted Sz-TE2 Orf contained 411 bps (without the stop codon) and the translation encoded a 15.6 kDa protein with 137 amino acids. A BLAST analysis of the nucleotide sequence against a proprietary *Schizochytrium* 20888 EST database identified three matches that confirmed the entire Orf from the ATG to a TGA stop codon. The Orf nucleotide sequence is show in SEQ ID NO:5 and the translation is shown in SEQ ID NO:1. As indicated, BLAST analysis of the Sz-TE2 protein sequence reveals homology to 4-hydroxybenzoyl-CoA-like thioesterases.

Sz-TE3: The Sz-TE3 Orf annotated in the proprietary genome sequence database was predicted to encode 881 amino acids and the coding region to contain 3 introns within the overall length of the gene (start to stop) of 6,800 bp. A query of the proprietary *Schizochytrium* 20888 EST database with that entire sequence revealed that only the 3' portion had matches. The eight ESTs identified in the BLAST search formed a contig that included an Orf (from ATG to a TGA stop) whose sequence matched that of the genomic data. The Orf for the region confirmed by the ESTs contained 963 nucleotides (without the stop codon) which encoded a 36.6 kDa protein with 321 amino acids. The Sz-TE3 Orf nucleotide sequence is show in SEQ ID NO:6 and the translation is shown in SEQ ID NO:2. BLAST analysis of the Sz-TE3 protein sequence also reveals homology to 4-hydroxybenzoyl-CoA-like thioesterases—but in this case there are two similar regions: i.e., two adjacent regions, both with homology to the 4-hydroxybenzoyl-CoA-like thioesterases.

Example 5

The following example describes the verification that candidate proteins, Sz-TE2 and Sz-TE3, are indeed associated with enhancement of in vitro *Schizochytrium* 20888 PUFA synthase activity and suggest that they have optimal activity when expressed together.

Construction of *E. coli* expression plasmids containing Sz-TE2 and Sz-TE3: The Orfs encoding Sz-TE2 and Sz-TE3 were cloned separately and together into two Novagen Duet vectors: pETDuet™ (carrying the Amp resistance marker) and pCOLADuet™ (carrying the Kan resistance marker). In both cases, the Sz-TE2 Orf was cloned into the MCS-2 and the Sz-TE3 was cloned into the MCS-1. The final nucleotide sequences Orfs for both Orfs in the constructs were identical to the native sequences. The Novagen Duet plasmids utilize the T7 expression system and require host cell lines containing an inducible T7 polymerase, e.g., BLR(DE3) or BL21(DE3). IPTG (0.5 mM) was used to induce expression of the genes.

Expression of Sz-TE2 and Sz-TE3 in *E. coli*—testing for protein solubility: A test of solubility of the Sz-TE2 and Sz-TE3 proteins in *E. coli* was carried out by expressing the proteins, either separately or together, collecting the induced cells and using the Novagen "BugBuster®" reagent and centrifugation protocol to separate 'soluble' proteins from cell debris and non-soluble proteins. Samples of the whole cells and the soluble and non-soluble fractions were treated with SDS and analyzed by SDS-PAGE. A Coomassie Blue stained gel in which the proteins present in whole cells and the 'soluble' and 'non-soluble' fractions from the several *E. coli* strains had been separated was examined. This revealed that a well stained protein band associated with Sz-TE2 was present in the soluble fractions both when expressed by itself and when co-expressed with Sz-TE3. In contrast, when Sz-TE3 was expressed by itself, very little protein was detected in the soluble fraction while a prominent band was present in the non-soluble fraction. When Sz-TE3 was co-expressed with Sz-TE2, the majority of the Sz-TE3 protein was now detected in the soluble fraction. These data suggest an interaction between Sz-TE3 and Sz-TE2 which increases the solubility of Sz-TE3. They also indicate that determination of the activity of Sz-TE3 when expressed by itself in this particular *E. coli* system may be compromised by its lack of solubility.

Use of *E. coli* expressed Sz-TE2 and Sz-TE3 in the PUFA synthase activity enhancement assay: The Orfs encoding *Schizochytrium* 20888 EF-X candidates Sz-TE2 and Sz-TE3 were cloned separately and together into Novagen Duet vectors as described above. *E. coli* strains containing the TE constructs were grown in LB medium at 32° C. Expression was induced by addition of IPTG and the incubation continued for 3 to 5 hours. Cells were collected by centrifugation and resuspended in Buffer K (50 mM NaPO$_4$ pH6.8, 10% glycerol) and lysed using a French Pressure cell (16,000 psi—two passes). Aliquots of the homogenates were either stored directly, or centrifuged (20,000×g×20 min) to yield a supernatant fraction (S20) before being aliquoted and stored at −80° C. The homogenates and supernatant fractions were diluted 6× in Buffer K prior to being combined with the separately prepared homogenate of JK824 (expressing the *Schizochytrium* 20888 PUFA synthase genes and HetI) for the enhancement assay. In some assays, equal volumes of extracts from strains expressing Sz-TE2 or Sz-TE3 were combined—if tested alone, Buffer K was used to equalize the volumes. The reactions are started by addition of $^{14}$C-malonyl CoA plus NADPH and run for 20 to 30 min at room temperature (~21° C.) then stopped by addition of isopropanol/acetic acid. Neutral lipids were extracted using a hexane/isopropanol solution and separated by normal phase TLC (Metz et al., 2009, Plant Physiology and Biochemistry, 47:472-478). FIG. 1 shows the results of the activity assays when the extracts (homogenates or supernatant fractions) from these strains, or Buffer K, were combined with extracts from JK824. 2H and 3H refer to Sz-TE2 and Sz-TE3, respectively, in homogenates fractions. 2S and 3S refer to Sz-TE2 and Sz-TE3, respectively, in supernatant fractions. The data in the figure indicate that while the addition of Sz-TE2 or Sz-TE3 alone did not enhance the PUFA synthase activity, significant enhancement (6 to 9 fold) was obtained when they were combined. Additionally, the enhancing effect was observed with both the homogenate and the supernatant fractions. These results confirm that the candidates, Sz-TE2 and Sz-TE3, are indeed associated with the EF-X activity and that both are likely to be required for that activity.

Example 6

The following example describes the effects of inactivation of the Sz-TE2 or Sz-TE3 genes in the Quad-KO strain of *Schizochytrium* 20888 on the EF-X activity in extracts derived from those strains. The results indicate that the Sz-TE2 and Sz-TE3 genes encode the primary factors associated with the in vitro PUFA synthase enhancing activity in extracts of *Schizochytrium* 20888.

Figure 2:
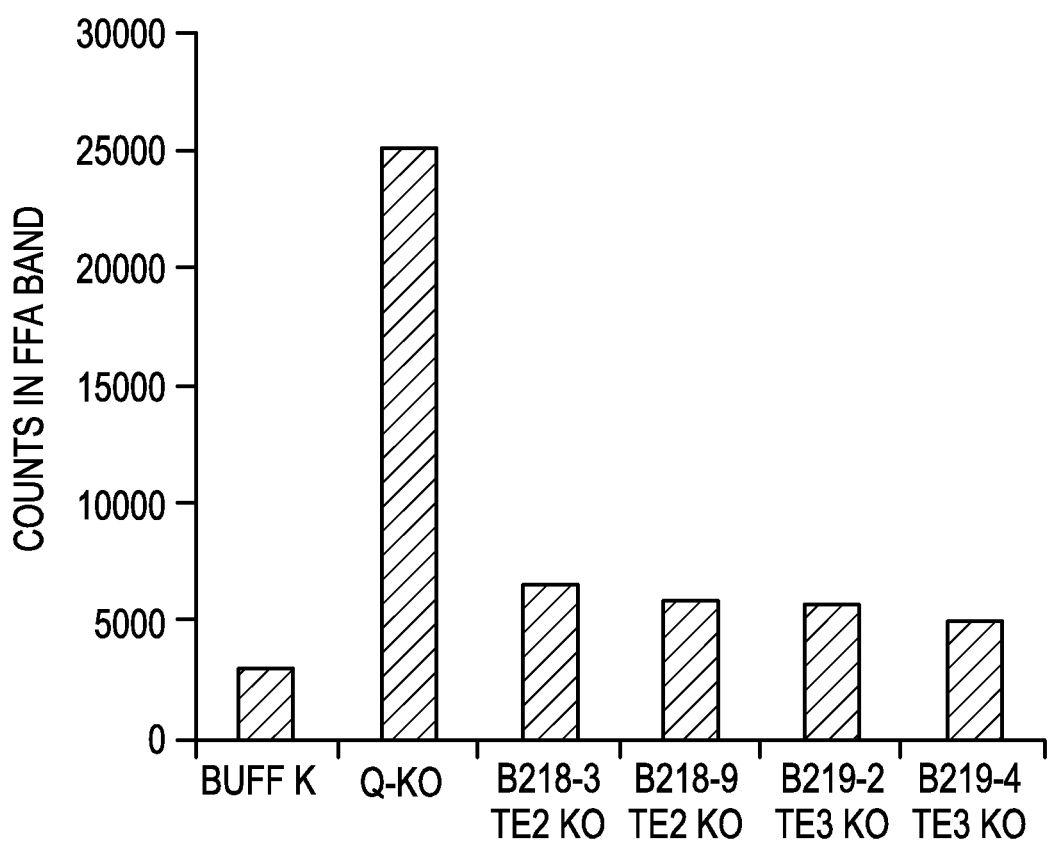
FIG. 2 is a diagram showing the result of an in vitro PUFA synthase activity enhancing assay using extracts from the *Schizochytrium* 20888 Quad-KO strain or extracts from cells derived from that strain in which either Sz-TE2 or Sz-TE3 have been inactivated.

Construction of Sz-TE2 and Sz-TE3 KO plasmid cassettes: The in vitro PUFA synthase enhancing activity was originally characterized by combining extracts from *E. coli* with extracts prepared from the Quad-KO strain of *Schizochytrium* 20888. In this strain, the genes encoding the FAS protein and the three subunits of the PUFA synthase were inactivated by replacement of the coding regions with antibiotic resistance cassettes. For inactivation of the SzTE genes in the Quad-KO strain, plasmids were constructed in which the coding regions of either the Sz-TE2 or Sz-TE3 were replaced with another antibiotic resistance cassette (paromomycin). Transformation of the Quad-KO strain was carried out using the Biolistic system (Roessler et al., 2006 U.S. Pat. No. 7,001,772) and paromomycin resistant colonies were selected on plates supplemented with both short chain saturated fatty acids and with DHA. The structures of the Sz-TE2 and Sz-TE3 loci in the putative KO strains were verified by sequencing of cloned PCR fragments generated by using primers targeted to regions outside of the DNA flanking used in the transformation cassettes. Two independent transformants for each of the Sz-TE2 and Sz-TE3 KOs were grown in liquid medium, the cells collected by centrifugation and resuspended in Buffer K. Cell homogenates were prepared by shaking with glass beads which were then separated from the homogenates by filtration. The homogenates were then centrifuged (20,000×g×10 min) to yield a fraction (S20) that was used in the in vitro PUFA synthase activity enhancement assay. FIG. 2 shows the results of the those assays along with the activity of the *E. coli* extract itself (combined with Buffer K) and a sample in which a S20 fraction from the parent Quad-KO strain has been added. The addition of the Quad-KO extract resulted in an ~8-fold increase in PUFA synthase activity in the assay (a typical enhancement of activity observed with this type of extract). Use of the extracts from strains in which either the Sz-TE2 or the Sz-TE3 gene have been disrupted resulted in only a minor increase in the *E. coli* expressed PUFA synthase activity. These data demonstrate that Sz-TE2 and Sz-TE3 are responsible for the majority of the enhancing activities observed in extracts of *Schizochytrium* 20888 cells and that expression of both Sz-TE2 and Sz-TE3 genes are needed for the appearance of the enhancing activity.

Example 7

The following example describes the effects of inactivation of Sz-TE2 and Sz-TE3 and both genes in *Schizochytrium* 20888. The results reveal the in vivo roles of Sz-TE2 and Sz-TE3: although DHA and DPAn-6 still accumulate in the KO strain, their levels are significantly reduced.

The Sz-TE2 and Sz-TE3 proteins were identified using an in vitro PUFA synthase enhancement assay. The potential role of these proteins in PUFA production and accumulation in cells of *Schizochytrium* 20888 was investigated by inactivation of the corresponding genes in the wild type *Schizochytrium* 20888 background. Sz-TE2 and Sz-TE3 KO constructs were made using the methods described above. For this experiment, the Sz-TE2 coding region was replaced with a paromomycin resistance cassette and the Sz-TE3 with a Zeocin resistance cassette. Sz-TE2 and Sz-TE3 were inactivated separately in that background to generate Sz-TE2 and Sz-TE3 KO strains. Double Sz-TE KO strains were then created by transformation with the second KO construct. Antibiotic resistant transformants that grew on plates that were not supplemented with DHA were obtained for both the single and double KO genes. Insertional replacements of the TE genes with the antibiotic resistance cassettes for several of the KOs were confirmed by cloning and sequencing of PCR product using primers targeted to DNA regions located outside of the flanking DNA used for the KO constructs. Cells of the wild type strain as well as examples of the single and double TE KO strains were grown, collected and their fatty acid profiles determined. Table I-A shows typical fatty acid profiles, shown as the % of total FAMEs, obtained for these strains while Table I-B shows those profiles expressed as the mg of the individual FAMEs per gram of dried biomass. It can be seen that all three versions of the Sz-TE KO strains (Sz-TE2 KO, Sz-TE3 KO and the double KO) have fairly similar fatty acid profiles. Although all of the strains accumulate DHA, the amounts of that fatty acid have been significantly reduced relative to the wild type. In the example shown, DHA decreased from ~40% of total FAME in the wild type to ~34% in the TE2 KO and to ~30% in the TE3 and double KOs. The higher amount of DHA detected in the Sz-TE2 KO strain, relative to those in which Sz-TE3 has been inactivated, suggests that Sz-TE3 may have some activity on its own. Additionally, the ratio of DHA to DPAn-6 in all of the strains has been lowered, from ~2.3 in the parental strain to <2 in all of the TE KO strains. Although the DPAn-6 level, as a % of total FAME, has not been significantly altered in the KO strains, the amount produced—when calculated as mg of DPAn-6 FAME per gram of biomass has been reduced. Although the reduction in DHA and DPAn-6 in the KO strains has been partially compensated by an increase in other fatty acids (derived from the FAS), the total mg FAME is still reduced (Table I-B). These data indicate that while the products of the PUFA synthase (DHA and DPAn-6) still accumulate in *Schizochytrium* 20888 strains in which the Sz-TE2 and or Sz-TE3 genes have been inactivated, the levels of those two PUFAs are higher when both genes are intact. The data provide a rationale for why DHA and DPAn-6 are observed to accumulate when the *Schizochytrium* 20888 PUFA synthase (along with an appropriate PPTase) is expressed in heterologous organisms and suggest that co-expression of Sz-TE2 plus Sz-TE3 may be a means to increase the accumulation in those cells.

TABLE I-A

| Fatty acid | 20888 WT | X022-1 SzTE2 KO | X023-17 SzTE3 KO | X024-2 SzTE2 + 3 KO | X024-4 SzTE2 + 3 KO |
|---|---|---|---|---|---|
| C14:0* | 4.9 | 3.2 | 4.3 | 6.0 | 5.4 |
| C16:0* | 29.6 | 30.3 | 34.6 | 40.1 | 35.8 |
| C16:1* | 0.9 | 2.4 | 3.4 | 2.5 | 2.5 |
| C18:0* | 0.9 | 1.6 | 1.8 | 1.6 | 1.5 |
| C18:1 N7 | 0.6 | 2.8 | 3.8 | 2.4 | 2.8 |
| C20:5 N3* | 1.0 | 1.5 | 1.1 | 0.9 | 0.9 |
| C22:4 N9 | 0.7 | 1.4 | 1.3 | 1.0 | 1.1 |
| C22:5 N6* | 17.7 | 18.5 | 16.3 | 14.3 | 16.7 |
| C22:6 N3* | 40.4 | 34.3 | 29.8 | 27.9 | 29.2 |
| DHA:DPAn6 | 2.3 | 1.9 | 1.8 | 1.9 | 1.7 |
| DHA + DPAn6 | 58.1 | 52.8 | 46.1 | 42.2 | 45.8 |

Table I-A shows fatty acid profiles—as % of total FAME—of wild type *Schizochytrium* 20888 and strains in which the following genes have been inactivated by insertional mutagenesis: Sz-TE2 (X022-1) or Sz-TE3 (X023-17) or both Sz-TE2 and Sz-TE3 (X024-2 and X024-4). Only those fatty acids with levels>1% of the total FAMEs are shown.

TABLE I-B

| Fatty Acid | 20888 WT | X022-1 SzTE2 KO | X023-17 SzTE3 KO | X024-2 SzTE2 + 3 KO | X024-4 SzTE2 + 3 KO |
|---|---|---|---|---|---|
| C14:0* | 14.1 | 7.2 | 10.1 | 15.4 | 13.5 |
| C16:0* | 85.7 | 67.3 | 81.3 | 103.0 | 88.8 |
| C16:1* | 2.5 | 5.3 | 7.9 | 6.5 | 6.1 |
| C18:0* | 2.6 | 3.6 | 4.2 | 4.2 | 3.8 |
| C18:1 N7 | 1.7 | 6.2 | 9.0 | 6.2 | 7.0 |
| C20:5 N3* | 2.9 | 3.3 | 2.7 | 2.4 | 2.3 |
| C22:4 N9 | 2.0 | 3.2 | 3.0 | 2.6 | 2.6 |
| C22:5 N6* | 51.4 | 41.1 | 38.3 | 36.9 | 41.3 |
| C22:6 N3* | 116.9 | 76.1 | 70.0 | 71.7 | 72.2 |
| Sum FAME | 289.4 | 222.0 | 235.3 | 257.0 | 247.8 |

Table I-B shows fatty acid profiles—mg FAME per gram of dried biomass—of wild type *Schizochytrium* 20888 and strains in which the following genes have been inactivated by insertional mutagenesis: Sz-TE2 (X022-1) or Sz-TE3 (X023-17) or both Sz-TE2 and Sz-TE3 (X024-2 and X024-4). Only those fatty acids listed in Table I-A are shown.

Example 8

The following example describes the effect on fatty acid profiles of co-expression of Sz-TE2 and Sz-TE3 in *E. coli* expressing the *Schizochytrium* 20888 PUFA synthase and HetI. The data indicate that accumulation of the products of the PUFA synthase (DHA and DPAn-6) can be increased by co-expression of Sz-TE2 plus Sz-TE3.

Expression of the *Schizochytrium* 20888 PUFA synthase subunits along with HetI in *E. coli* results in accumulation of DHA and DPAn-6 (see Hauvermale et al., 2008, Lipids, 41:739-747 for details). Additionally, it was determined that all of the PUFAs in those cells were in the free fatty acid form, as opposed to being esterified (e.g., as components of phospholipids). This observation was consistent with the results of in vitro activity assays of extracts from these cells; i.e., the products of the *Schizochytrium* 20888 PUFA synthase reactions were detected as free fatty acids. The 'enhancement' of the free fatty acid products of the in vitro PUFA synthase activity formed the basis of the assay developed for identification of the EF-X factors. The fatty acid profiles of *E. coli* strains in which the Sz-TE2 and Sz-TE3 proteins were co-expressed, either separately or together, along with the *Schizochytrium* 20888 PUFA synthase system were also determined. *E. coli* strain JK824 (expressing the *Schizochytrium* 20888 PUFA synthase subunits and HetI) were transformed with the pCOLA™ duet vector containing either Sz-TE2 (TE2) or Sz-TE3 (TE3) or both Sz-TE2+Sz-TE3 (TE2+TE3). Verified transformants were grown at 32°

TABLE II-A

| Fatty Acid | JK824 | TE2 JK1350 | TE2 JK1351 | TE3 JK1346 | TE3 JK1347 | TE2 + 3 JK1349 | TE2 + 3 JK1348 |
|---|---|---|---|---|---|---|---|
| C12:0* | 5.6 | 5.4 | 5.4 | 5.0 | 5.8 | 4.5 | 5.2 |
| C14:0* | 3.6 | 3.8 | 4.1 | 3.3 | 4.2 | 3.1 | 3.8 |
| C16:0* | 17.8 | 18.2 | 20.5 | 17.1 | 19.5 | 15.6 | 17.5 |
| C16:1* | 8.1 | 9.4 | 6.2 | 7.5 | 7.3 | 7.5 | 6.2 |
| Unknown 1 | 6.0 | 6.1 | 6.9 | 6.2 | 6.8 | 5.3 | 6.3 |
| C18:1 N7 | 26.6 | 26.8 | 23.6 | 26.1 | 24.2 | 23.2 | 20.9 |
| Unknown 3 | 5.1 | 4.3 | 7.3 | 6.6 | 5.2 | 5.0 | 5.3 |
| Unknown 4 | 7.8 | 7.2 | 8.0 | 7.6 | 8.0 | 7.0 | 7.5 |
| C22:5 N6* | 4.6 | 5.0 | 3.4 | 4.9 | 4.0 | 6.4 | 5.7 |
| C22:6 N3* | 9.0 | 8.7 | 8.4 | 9.6 | 8.8 | 17.4 | 15.9 |
| DHA + DPAn6 | 13.6 | 13.7 | 11.8 | 14.5 | 12.8 | 23.9 | 21.5 |
| DHA/DPAn6 | 2.0 | 1.7 | 2.5 | 2.0 | 2.2 | 2.7 | 2.8 |

Table II-A shows fatty acid profiles—as % of total FAME—of *E. coli* strain JK824 (expressing the *Schizochytrium* 20888 PUFA synthase subunits and HetI) and of strains expressing either Sz-TE2 (TE2) or Sz-TE3 (TE3) or both (TE2+3) in the JK824 background. Only those fatty acids with levels>1% of the total FAMEs are shown.

C. in 765 medium supplemented with 10% (wt/vol) glycerol (Hauvermale et al., 2008, Lipids, 41:739-747). The cells were harvested 20 hrs after induction with IPTG, washed with 50 mM Tris pH 7.5, freeze dried and the fatty acids converted to FAMEs and analyzed by GC. The results are shown in the following Tables.

TABLE II-B

| Fatty Acid | JK824 | TE2 JK1350 | TE2 JK1351 | TE3 JK1346 | TE3 JK1347 | TE2 + 3 JK1349 | TE2 + 3 JK1348 |
|---|---|---|---|---|---|---|---|
| C12:0* | 3.0 | 3.0 | 2.7 | 2.8 | 3.1 | 2.7 | 3.2 |
| C14:0* | 1.9 | 2.1 | 2.1 | 1.9 | 2.3 | 1.9 | 2.3 |
| C16:0* | 9.5 | 10.0 | 10.4 | 9.6 | 10.6 | 9.4 | 10.7 |
| C16:1* | 4.3 | 5.2 | 3.1 | 4.2 | 3.9 | 4.5 | 3.8 |
| Unknown 1 | 3.2 | 3.4 | 3.5 | 3.5 | 3.7 | 3.1 | 3.8 |
| C18:1 N7 | 14.2 | 14.7 | 11.9 | 14.7 | 13.0 | 13.9 | 12.7 |
| Unknown 3 | 2.7 | 2.4 | 3.7 | 3.7 | 2.8 | 3.0 | 3.2 |
| Unknown 4 | 4.2 | 4.0 | 4.0 | 4.2 | 4.3 | 4.2 | 4.6 |
| C22:5 N6* | 2.5 | 2.8 | 1.7 | 2.8 | 2.2 | 3.9 | 3.5 |
| C22:6 N3* | 4.8 | 4.8 | 4.2 | 5.4 | 4.7 | 10.5 | 9.7 |
| Sum FAME | 53.2 | 55.0 | 50.4 | 56.1 | 53.9 | 60.0 | 60.9 |
| DHA + DPAn6 | 7.3 | 7.5 | 5.9 | 8.2 | 6.9 | 14.4 | 13.1 |

Table II-B shows fatty acid profiles—as mg of FAME/gram dried biomass—of the *E. coli* strains shown in Table II-A. Only those fatty acids included in Table II-A are shown.

The data in Table II-A indicate that co-expression of either Sz-TE2 or Sz-TE3 alone with the *Schizochytrium* 20888 PUFA synthase system in *E. coli* does not significantly alter the fatty acid profiles (as % of total FAME) relative to the parental strain (JK824). In contrast, expression of Sz-TE2 and Sz-TE3 together results in an approximately two-fold increase in the amount of DHA in those cells. Interestingly, there is also an increase in the amount of DPAn-6, but it is less than for DHA, resulting in an increase in the ratio of DHA to DPAn-6—from ~2.0:1 to ~2.7:1. This higher ratio is closer to what is typically observed in oil from *Schizochytrium* 20888 itself The data shown in Table II-B indicate that the increase in % PUFA observed when Sz-TE2 and Sz-TE3 are both expressed is accompanied by an increase in accumulation of the total mg of FAME per gram of biomass. Furthermore that increase is specifically associated with an increase in mg of DHA and DPAn-6 while the amounts of other fatty acids are relatively unchanged. Previous analysis indicated that the products of the PUFA synthase accumulate as free fatty acids in *E. coli*, and it is likely that additional PUFAs in these cells are also present as free fatty acids rather than being incorporated into cellular membranes.

Example 9

The following example describes the effect on fatty acid profiles of co-expression of Sz-TE2 and Sz-TE3 in yeast expressing the *Schizochytrium* 20888 PUFA synthase and HetI. The data indicate that accumulation of the products of the *Schizochytrium* 20888 PUFA synthase (DHA and DPAn-6) can be increased by co-expression of Sz-TE2 plus Sz-TE3. They also indicate that Sz-TE3 has some activity when expressed without Sz-TE2.

Cloning of Sz-TE2 and Sz-TE3 Orfs into yeast expression vectors: Expression of the *Schizochytrium* 20888 PUFA synthase (PFA 1, 2 and 3) along with HetI in yeast results in accumulation of DHA and DPAn-6 in those cells (Metz et al., US Patent Application Publication No. 2013-0150599). One of the strains created for expressing this system contained the genes in the following vectors: PFA1 in a pYES-Leu vector (the Orf codons were modified for yeast expression), PFA2 in a pYES3-Tryp vector (the Orf codons were modified for yeast expression) and PFA3 and HetI in a pESC-Ura vector (the native Orf sequences were used for both genes). To test the effects of co-expression of the enhancing factor candidates with the *Schizochytrium* 20888 PUFA synthase—Sz-TE2 and Sz-TE3 coding regions were cloned into a pESC-His vector, either separately or together. Sz-TE2 was cloned behind the Gal 1 promoter (as a BamHI-XhoI fragment) while Sz-TE3 was cloned behind the Gal 10 promoter (as a EcoRI-NotI fragment). Both DNA fragments retained the native Orf nucleotide sequences.

FAME profiles of yeast strains expressing the *Schizochytrium* 20888 PUFA synthase system and Sz-TE2 and Sz-TE3: Yeast strains expressing either the active *Schizochytrium* 20888 PUFA synthase (subunit genes plus HetI) alone or also containing either Sz-TE2 or Sz-TE3, alone or together, were grown on appropriate media. Expression of the transgenes was induced by resuspension of washed cells in media containing galactose. The cells were grown for 20 hrs at 30° C. after induction then collected by centrifugation, freeze dried and their fatty acids converted to FAMEs using acidic methanol and analyzed by GC. The FAME profiles of the various strains are shown in Table III (as % of total FAME). The control strain (with just the PUFA synthase genes plus HetI) produced DHA and DPAn-6 at levels consistent with previous observations (Metz et al., US Patent Application Publication No. 2013-0150599), i.e., 2.9% DHA and 1.8 or 1.9% DPAn-6. Co-expression of Sz-TE2 alone did not increase the PUFA levels. Co-expression of Sz-TE3 alone resulted in an ~1.5×increase in PUFA accumulation but did not alter the DHA to DPAn-6 ratio. Co-expression of Sz-TE2 and Sz-TE3 together resulted in an ~1.6×increase in PUFA accumulation with an ~1.9×increase in DHA level. Additionally, the DHA to DPAn-6 ratio in the cells co-expressing the Sz-TE2 plus Sz-TE3 increased from ~1.5 to ~2.7. As in the case of expression in *E. coli*, the Sz-TE2 by itself did not result in an increase in PUFA accumulation. In contrast to the *E. coli* result, Sz-TE3 by itself did increase the accumulation both DHA and DPAn-6 in yeast. The apparent lack of solubility of Sz-TE3 (when expressed without Sz-TE2) in *E. coli* may account for the different result in obtained yeast. it is apparent that the outcome can be affected by the heterologous host utilized for expression. The increase in the DHA:DPAn-6 ratio is again observed when Sz-TE2 and Sz-TE3 are both expressed (from ~1.5 to ~2.7).

TABLE III

| % FAME Fatty Acid | 24 hrs BRY4.11-3 | BRY4.11-4 | TE2 YMR1-3 | TE2 YMR1-4 | TE3 YMR2-3 | TE3 YMR2-4 | TE2 + 3 YMR3-3 | TE2 + 3 YMR3-4 |
|---|---|---|---|---|---|---|---|---|
| C12:0* | 1.7 | 1.6 | 2.1 | 2.3 | 1.8 | 1.9 | 2.1 | 2.1 |
| C14:0* | 1.4 | 1.3 | 1.7 | 1.8 | 1.3 | 1.3 | 1.6 | 1.6 |
| C14:1* | 0.4 | 0.4 | 0.5 | 0.6 | 0.4 | 0.4 | 0.4 | 0.5 |
| C16:0* | 17.5 | 17.1 | 19.0 | 18.9 | 18.3 | 18.5 | 18.5 | 18.3 |
| C16:1* | 41.5 | 41.4 | 43.5 | 45.7 | 39.7 | 40.4 | 40.8 | 41.8 |
| C18:0* | 6.1 | 6.1 | 5.8 | 5.2 | 6.1 | 6.0 | 5.6 | 5.2 |
| C18:1 N9* | 25.1 | 25.5 | 22.8 | 21.9 | 23.2 | 22.9 | 21.9 | 21.4 |
| C18:1 N7* | 1.0 | 1.0 | 0.9 | 0.8 | 0.9 | 0.8 | 0.7 | 0.7 |
| C22:5 N6* | 1.9 | 1.8 | 1.2 | 0.9 | 2.6 | 2.7 | 2.0 | 2.1 |
| C22:6 N3* | 2.9 | 2.9 | 1.9 | 1.6 | 4.8 | 4.1 | 5.5 | 5.6 |
| DHA + DPAn6 | 4.7 | 4.7 | 3.1 | 2.5 | 7.4 | 6.8 | 7.5 | 7.7 |
| DHA/DPAn6 | 1.5 | 1.6 | 1.6 | 1.8 | 1.8 | 1.5 | 2.7 | 2.7 |

Table III shows fatty acid profiles—as % of total FAME—of control yeast strains (BRY4.11—expressing the Schizochytrium 20888 PUFA synthase, PFA 1, 2, and 3, and HetI) and strains expressing either Sz-TE2 or Sz-TE3 or both in the parental (BRY4.11) background. Only those fatty acids with levels>1% of the total FAMEs are shown.

Example 10

This example demonstrates that homologs of Sz-TE2 and Sz-TE3 can be readily identified in another Thraustochytrid that utilizes a PUFA synthase.

Schizochytrium 9695 contains a PUFA synthase homologous to that found in Schizochytrium 20888 (Apt et al., U.S. Patent Application Publication No. 2010-0266564). A draft whole genome sequence of this organism was generated and assembled into contigs. A translated BLAST (tblastn) search was carried out against a database set containing all of the assembled contigs using the Sz-TE2 and Sz-TE3 amino acid sequences as queries. In both cases only 2 contigs were identified with significant homology to the query sequences—and they were the same contigs in both cases (in reverse order). The appropriate open reading frames were identified and the nucleotide sequences and their predicted translations are listed. The amino acid homolog to Sz-TE2 has been designated B-TE2, the amino acid homolog to Sz-TE3 has been designated B-TE3. The nucleotide sequences of these two Orfs along with the predicted translations are shown in the 'Sequence Listing' and are described below.

The nucleotide sequence encoding B-TE2 and the predicted translation: The nucleotide sequence of the predicted Orf contained 468 bps (without the stop codon) and the translation encoded a 17.36 kDa protein with 156 amino acids.

The nucleotide sequence encoding B-TE3 and the predicted translation: The nucleotide sequence of the predicted Orf contained 963 bps (without the stop codon) and the translation encoded a 36.5 kDa protein with 321 amino acids.

Alignment of Sz-TE2 and Sz-TE3 amino acid sequences with the B-TE homologs: FIG. 3A shows the alignment of Sz-TE2 with B-TE2. The identical residues in this alignment are shown in light grey and the conservative changes in darker grey, respectively. Using Sz-TE2 as the reference, 52 in 137 amino acids are identical (38.0%) and there are 78 in 137 positives (identical plus conservative changes) (56.9%). The B-TE2 sequence has an additional region rich in serines and glycines in the middle of the protein (shown as a gap in the alignment).

Figure 3B:
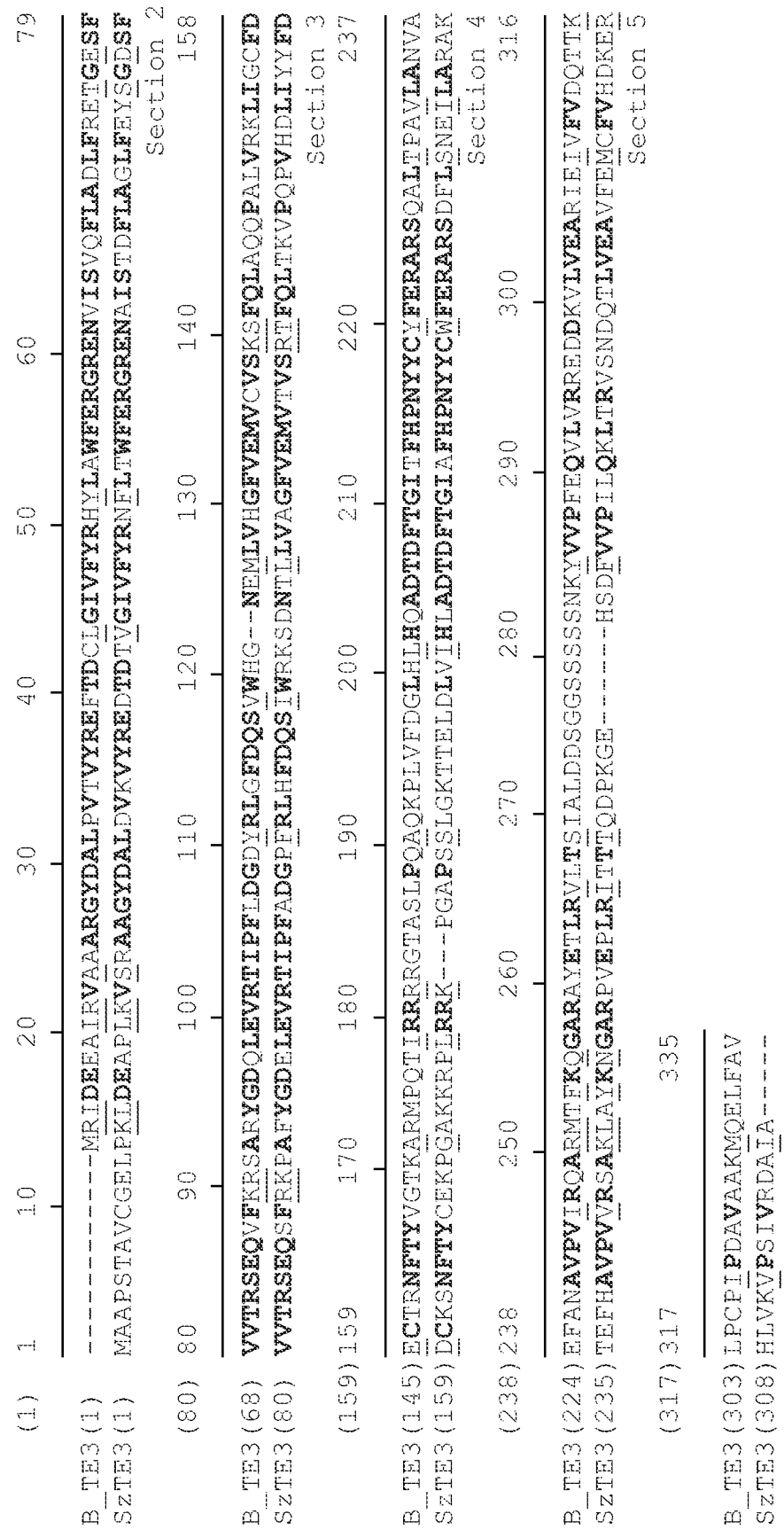
FIG. 3B is a diagram showing the alignment between the amino acid sequence of enhancing factor proteins B-TE3 and Sz-TE3.

FIG. 3B shows the alignment of Sz-TE3 with B-TE3. Both Sz-TE3 and B-TE3 contain 321 amino acids. In this alignment, 155 in 321 amino acids are identical (48.3%) and there are 192 in 321 positives (59.8%). As in the case of B-TE2, the B-TE3 sequence has an additional region rich in serine and glycines in the middle of the protein (shown as a gap in the alignment).

Example 11

This example demonstrates that B-TE2 and B-TE3 can enhance the activity of the Schizochytrium 20888 PUFA synthase in an in vitro assay. It suggests that the EF-Xs may play a general role of enhancing PUFA synthase activities.

Construction of E. coli expression plasmids containing B-TE2 and B-TE3 Orfs: The same basic strategy used for cloning Sz-TE2 and Sz-TE3 was employed for the B-TE homologs. Orfs encoding B-TE2 and B-TE3 were cloned separately and together into the two Novagen Duet vectors: pETDuet™ (carrying the Amp resistance marker) and pCO-LADuet™ (carrying the Kan resistance marker). In both cases, the B-TE2 Orf was cloned into the MCS-1 and B-TE3 was cloned into the MCS-2. The final Orfs for both genes in the constructs were identical to the native Orfs listed above.

Expression of B-TE2 and B-TE3 in E. coli—testing for protein solubility: The same strategy used for assessing the solubility of the Sz-TE2 and Sz-TE3 proteins in E. coli was employed for the B-TE homologs. Cells containing plasmids with B-TE2 and B-TE3, either separately or together, were grown on LB medium at 32° C. Synthesis of the proteins was induced by addition of IPTG (0.5 mM) and incubation was continued for 3 to 5 hrs. The cells were collected by centrifugation and the Novagen "BugBuster®" reagent (and centrifugation protocol) was used to separate soluble proteins from cell debris and non-soluble proteins (presumably sequestered in inclusion bodies). Samples of the whole cells and the soluble and non-soluble fractions were treated with SDS and analyzed by SDS-PAGE. Bands associated with B-TE2 and B-TE3 were readily detected in the whole cell extracts, with the B-TE3 being very highly expressed. Comparison of the proteins in the soluble and the non-soluble fractions reveals that B-TE2, when expressed by itself, primarily partitions to the soluble fraction. In contrast, B-TE3 remains primarily in the insoluble fractions. When B-TE2 and B-TE3 are co-expressed in the same strain, most of both proteins are in the insoluble fractions, but a minor amount of both can be detected in the soluble fractions. These results are similar to what was observed for Sz-TE2 and Sz-TE3—but the insolubility of B-TE3 is more pronounced. As in the case of Sz-TE2 and Sz-TE3, these data suggest an interaction between B-TE2 and B-TE3 proteins which may increase the solubility of B-TE3 in the *E. coli* system.

Figure 4:
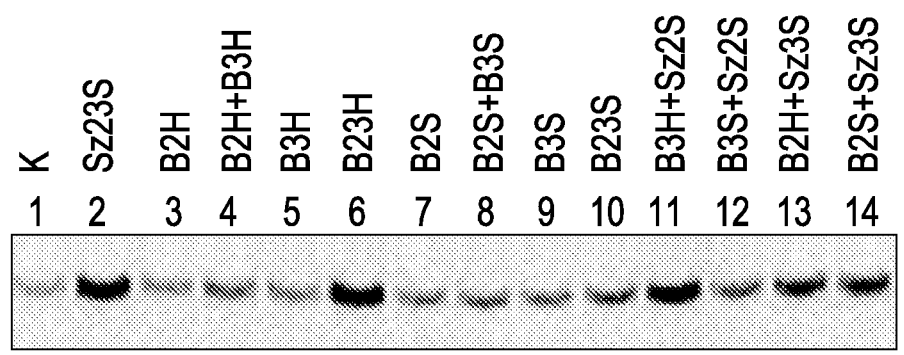
FIG. 4 is a diagram showing an in vitro PUFA synthase activity enhancing assay using separately expressed B-TE2 and B-TE3.
Figure 4:
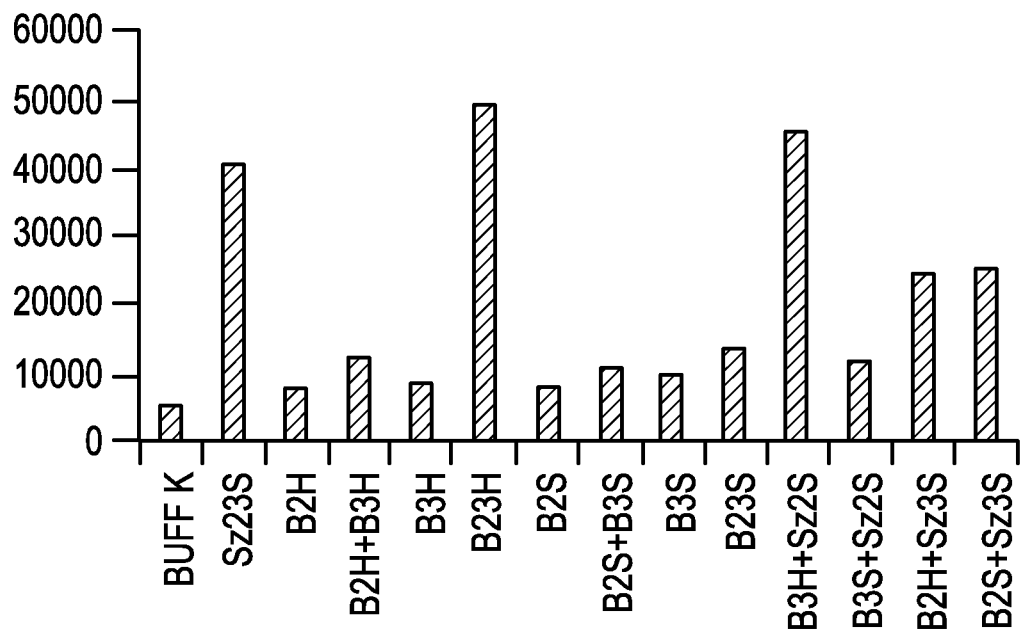

In vitro activity enhancement assays: addition of separately expressed B-TE2 and B-TE3 to the *Schizochytrium* 20888 PUFA synthase system: Aliquots of the cell homogenates and supernatant fractions from the *E. coli* strains described above were tested in the PUFA synthase in vitro activity assay. The extracts were mixed with a homogenate of *E. coli* strain JK824 (expressing the *Schizochytrium* 20888 Pfa 1, 2 and 3 plus HetI), and the assay run as described above. As for the assays of Sz-TE2 and Sz-TE3, the homogenates and supernatant fractions were diluted 6× in Buffer K prior to being combined with the separately prepared homogenate of JK824 in the enhancement assay (see Example 5, above, for additional details). FIG. 4 shows the results of these activity assays along with control assays (addition of buffer alone and addition of *E. coli* expressed Sz-TE2 and Sz-TE3). In FIG. 4, "B" refers to *Schizochytrium* 9695. "Sz" refers to *Schizochytrium* 20888. "2" refers to TE2. "3" refers to TE3. "S" refers to supernatant fraction. "H" refers to homogenate fraction. The data in the figure show that B-TE2 and B-TE3, when expressed together in *E. coli*, can significantly enhance the in vitro activity of the *Schizochytrium* 20888 PUFA synthase. This effect is most evident when the homogenate was used in the assay—the supernatant fraction from that strain was much less active. Additionally, the *Schizochytrium* 20888 and *Schizochytrium* 9695 derived B-TEs can be mixed—i.e., the B-TE2 can substitute for Sz-TE2 and B-TE3 can substitute for Sz-TE3. These data validate the selection of B-TE2 and B-TE3 as enhancing factor proteins.

While various embodiments of the present invention have been described in detail, it is apparent that modifications and adaptations of those embodiments will occur to those skilled in the art. It is to be expressly understood, however, that such modifications and adaptations are within the scope of the present invention.

What is claimed is:

1. A recombinant nucleic acid molecule comprising a nucleic acid sequence encoding a polypeptide that is at least 90% sequence identical to the amino acid sequence of SEQ ID NO:3 and an expression control sequence, wherein said nucleic acid sequence is heterologous to said expression control sequence, and where the polypeptide enhances polyunsaturated fatty acids (PUFA) production in a host cell when comparing to the PUFA production in a same host cell without the polypeptide.

2. The recombinant nucleic acid molecule of claim 1, wherein the polypeptide is at least 95% sequence identical to the amino acid sequence of SEQ ID NO:3.

3. The recombinant nucleic acid molecule of claim 1, wherein the polypeptide enhances the enzymatic activity of a polyunsaturated fatty acids (PUFA) synthase.

4. The recombinant nucleic acid molecule of claim 1, wherein the nucleic acid sequence encodes a polypeptide having the amino acid sequence of SEQ ID NO:3.

5. The recombinant nucleic acid molecule of claim 1, wherein the nucleic acid sequence is SEQ ID NO:7.

6. A recombinant nucleic acid molecule comprising a nucleic acid sequence encoding a polypeptide that is at least 90% sequence identical to the amino acid sequence of SEQ ID NO:2 or SEQ ID NO:4 and an expression control sequence, wherein said nucleic acid sequence is heterologous to said expression control sequence, and, where the polypeptide enhances polyunsaturated fatty acids (PUFA) production in a host cell when comparing to the PUFA production in a same host cell without the polypeptide.

7. The recombinant nucleic acid molecule of claim 6, wherein the polypeptide is at least 95% sequence identical to the amino acid sequence of SEQ ID NO:2 or SEQ ID NO:4.

8. The recombinant nucleic acid molecule of claim 6, wherein the polypeptide enhances the enzymatic activity of a PUFA synthase.

9. The recombinant nucleic acid molecule of claim 6, wherein the nucleic acid sequence encodes a polypeptide having the amino acid sequence of SEQ ID NO:2 or SEQ ID NO:4.

10. The recombinant nucleic acid molecule of claim 6, wherein the nucleic acid sequence is SEQ ID NO:6 or SEQ ID NO:8.

11. A host cell comprising the, recombinant nucleic acid molecule of any one of claims 1-3, 4-8, and 9-10.

12. The host cell of claim 11, wherein the host cell is a microorganism.

13. A genetically modified microorganism, wherein the microorganism has been genetically modified to express the recombinant nucleic acid molecule of any one of claims 1-3, 4-8, and 9-10.

14. The genetically modified microorganism of claim 13, wherein the microorganism endogenously expresses a PUFA synthase system, a phosphopantetheinyl transferase (PPTase), and/or an acyl-CoA synthetase (ACS).

15. The genetically modified microorganism of claim 14, wherein the microorganism is a Thraustochytriales microorganism.

16. The genetically modified microorganism of claim 15, wherein the microorganism is a *Schizochytrium*.

17. The genetically modified microorganism of claim 14, wherein the microorganism is a bacterium.

18. The genetically modified microorganism of claim 13, wherein the organism has been further genetically modified to exogenously express a PUFA synthase system, a phosphopantetheinyl transferase (PPTase), and/or an acyl-CoA synthetase (ACS).

19. The genetically modified microorganism of claim 18, wherein the PUFA synthase system comprises at least one functional domain from a PUFA synthase system from a Thraustochytriales microorganism.

20. The genetically modified microorganism of claim 19, wherein the PUFA synthase system comprises at least one functional domain from a PUFA synthase system from a *Schizochytrium*.

21. The genetically modified microorganism of claim 18, wherein the PUFA synthase comprises at least one functional domain from a PUFA synthase from a microorganism selected from the group consisting of *Schizochytrium* sp. American Type Culture Collection (ATCC) No. 20888, *Schizochytrium* sp. American Type Culture Collection (ATCC) No. PTA-9695, *Thraustochytrium* 23B American Type Culture Collection (ATCC) No. 20892, and a mutant of any of said microorganisms.

22. The genetically modified microorganism of claim 18, wherein the PUFA synthase comprises at least one functional domain from a PUFA synthase from a marine bacterium.

23. The genetically modified microorganism of claims 22, wherein the microorganism is a microalga, a yeast, or a bacterium.

24. The genetically modified microorganism of claim 18, wherein one or more nucleic acid sequences encoding the PUFA synthase has been optimized to improve the expression of the PUFA synthase in the microorganism.

25. The genetically modified microorganism of claim 24, wherein the microorganism comprises at least one polyunsaturated fatty acid (PUFA) selected from the group consisting of: DHA (C22:6, n-3), DPA (C22:5, n-6 or n-3), EPA (C20:5, n-3), ARA (C20:4, n-6), GLA (C18:3, n-6), and/or SDA (C18:4, n-3).

26. The genetically modified microorganism of claim 24, wherein the genetically modified microorganism comprises DHA, DPAn-6 and/or EPA.

27. The genetically modified microorganism of claim 13, wherein the amount of DHA, DPAn-6 and/or EPA produced in said genetically modified microorganism is higher than that is produced in the counterpart microorganism which none of the heterologous nucleic acid molecule of any one of claims 1-3, 4-8, and 9-10 is expressed.

28. The genetically modified microorganism of claim 13, wherein the ratio of DHA:DPAn-6 produced in said genetically modified microorganism is higher than that produced in the counterpart microorganism which none of the heterologous nucleic acid molecule of any one of claims 1-3, 4-8, and 9-10 is expressed.

29. The genetically modified microorganism of claim 27, wherein the microorganism is a microalga, a yeast, or a bacterium.

30. A method to produce at least one polyunsaturated fatty acid (PUFA), comprising growing the genetically modified microorganism of any one of claims 13 and 14-29.

* * * * *

```
                       SEQUENCE LISTING

<160> NUMBER OF SEQ ID NOS: 8

<210> SEQ ID NO 1
<211> LENGTH: 137
<212> TYPE: PRT
<213> ORGANISM: Schizochytrium sp

<400> SEQUENCE: 1

Met Thr Ala Gln Gly Gly Tyr Arg Ser Glu Met Leu Met Tyr Tyr Glu
1               5                   10                  15

Asp Thr Asp Leu Thr Gly Ala Val Tyr Ala Gly Asn Tyr Phe Lys Tyr
            20                  25                  30

Phe Glu Arg Ala Arg Asp Glu Ala Val Gly Ile Asp Val Leu Lys Thr
        35                  40                  45

Leu Met Asp Lys Glu Gly Leu Ala Leu Tyr Val Arg Lys Met Gly Glu
    50                  55                  60

Met Thr Phe Lys Gly Gly Ala Lys His Ala Asp Thr Leu Val Val Glu
65                  70                  75                  80

Ser Ser Val Glu Ala Pro Ser Asp Phe Arg Leu Val Phe Lys Gln Arg
                85                  90                  95

Ala Ser Val Lys Asp Arg Pro Glu Thr Ile Ile Val Glu Thr Asp Val
            100                 105                 110

Glu Val Val Cys Ile Asp Met Lys Thr Gln Arg Val Ala Lys Ile Pro
        115                 120                 125

Thr Gln Ile Arg Glu Ala Leu Arg Ile
    130                 135

<210> SEQ ID NO 2
<211> LENGTH: 321
<212> TYPE: PRT
<213> ORGANISM: Schizochytrium sp

<400> SEQUENCE: 2

Met Ala Ala Pro Ser Thr Ala Val Cys Gly Glu Leu Pro Lys Leu Asp
1               5                   10                  15

Glu Ala Pro Leu Lys Val Ser Arg Ala Arg Gly Tyr Asp Ala Leu Asp
            20                  25                  30

Val Lys Val Tyr Arg Glu Asp Thr Asp Thr Val Gly Ile Val Phe Tyr
        35                  40                  45
```

Arg Asn Phe Leu Thr Trp Phe Glu Arg Gly Arg Glu Asn Ala Ile Ser
50                  55                  60

Thr Asp Phe Leu Ala Gly Leu Phe Glu Tyr Ser Gly Asp Ser Phe Val
65                  70                  75                  80

Val Thr Arg Ser Glu Gln Ser Phe Arg Lys Pro Ala Phe Tyr Gly Asp
                85                  90                  95

Glu Leu Glu Val Arg Thr Ile Pro Phe Ala Asp Gly Pro Phe Arg Leu
            100                 105                 110

His Phe Asp Gln Ser Ile Trp Arg Lys Ser Asp Asn Thr Leu Leu Val
        115                 120                 125

Ala Gly Phe Val Glu Met Val Thr Val Ser Arg Thr Phe Gln Leu Thr
130                 135                 140

Lys Val Pro Gln Pro Val His Asp Leu Ile Tyr Tyr Phe Asp Asp Cys
145                 150                 155                 160

Lys Ser Asn Phe Thr Tyr Cys Glu Lys Pro Gly Ala Lys Lys Arg Pro
                165                 170                 175

Leu Arg Arg Lys Pro Gly Ala Pro Ser Ser Leu Gly Lys Thr Thr Glu
            180                 185                 190

Leu Asp Leu Val Ile His Leu Ala Asp Thr Asp Phe Thr Gly Ile Ala
        195                 200                 205

Phe His Pro Asn Tyr Tyr Cys Trp Phe Glu Arg Ala Arg Ser Asp Phe
210                 215                 220

Leu Ser Asn Glu Ile Leu Ala Arg Ala Lys Thr Glu Phe His Ala Val
225                 230                 235                 240

Pro Val Val Arg Ser Ala Lys Leu Ala Tyr Lys Asn Gly Ala Arg Pro
                245                 250                 255

Val Glu Pro Leu Arg Ile Thr Thr Gln Asp Pro Lys Gly Glu His
            260                 265                 270

Ser Asp Phe Val Val Pro Ile Leu Gln Lys Leu Thr Arg Val Ser Asn
        275                 280                 285

Asp Gln Thr Leu Val Glu Ala Val Phe Glu Met Cys Phe Val His Asp
    290                 295                 300

Lys Glu Arg His Leu Val Lys Val Pro Ser Ile Val Arg Asp Ala Ile
305                 310                 315                 320

Ala

<210> SEQ ID NO 3
<211> LENGTH: 156
<212> TYPE: PRT
<213> ORGANISM: Schizochytrium sp

<400> SEQUENCE: 3

Met Val Met Val Ala Glu Glu Lys Arg Ala His Glu Val Ala Val Gln
1               5                   10                  15

Leu Tyr Tyr Glu Asp Thr Asp Phe Ser Gly Phe Val His His Ala Asn
            20                  25                  30

Phe Leu Arg Tyr Phe Glu Arg Gly Arg Asp Glu Met Ile Gly Leu Pro
        35                  40                  45

Val Leu Lys Cys Leu Ala Gln Asp Asp Ser Ser Ser Ser Ser Ser Ala
50                  55                  60

Thr Ser Ile Gly Gly Gly Glu Pro Pro Val Ser Leu Phe Val His Lys
65                  70                  75                  80

Val His Glu Leu Ser Phe Lys Gly Arg Ala Arg His Gly Glu Met Leu
                85                  90                  95

```
Val Val Arg Ser Arg Val Val Lys Glu Ser Asp Phe Arg Leu Arg Phe
            100                 105                 110

Ala His Glu Ala Trp Val Gly Asn Thr Leu Val Ala Ser Gly Ser Met
            115                 120                 125

Asp Val Val Phe Leu Cys Gly Ser Val Asp Ala Arg Leu Val Lys Ile
            130                 135                 140

Pro Asn Ser Val Asp Val Ala Leu His Gly Tyr Tyr
145                 150                 155
```

<210> SEQ ID NO 4
<211> LENGTH: 321
<212> TYPE: PRT
<213> ORGANISM: Schizochytrium sp

<400> SEQUENCE: 4

```
Met Arg Ile Asp Glu Glu Ala Ile Arg Val Ala Ala Ala Arg Gly Tyr
1               5                   10                  15

Asp Ala Leu Pro Val Thr Val Tyr Arg Glu Phe Thr Asp Cys Leu Gly
            20                  25                  30

Ile Val Phe Tyr Arg His Tyr Leu Ala Trp Phe Glu Arg Gly Arg Glu
            35                  40                  45

Asn Val Ile Ser Val Gln Phe Leu Ala Asp Leu Phe Arg Glu Thr Gly
            50                  55                  60

Glu Ser Phe Val Val Thr Arg Ser Glu Gln Val Phe Lys Arg Ser Ala
65                  70                  75                  80

Arg Tyr Gly Asp Gln Leu Glu Val Arg Thr Ile Pro Phe Leu Asp Gly
                85                  90                  95

Asp Tyr Arg Leu Gly Phe Asp Gln Ser Val Trp His Gly Asn Glu Met
            100                 105                 110

Leu Val His Gly Phe Val Glu Met Val Cys Val Ser Lys Ser Phe Gln
            115                 120                 125

Leu Ala Gln Gln Pro Ala Leu Val Arg Lys Leu Ile Gly Cys Phe Asp
            130                 135                 140

Glu Cys Thr Arg Asn Phe Thr Tyr Val Gly Thr Lys Ala Arg Met Pro
145                 150                 155                 160

Gln Thr Ile Arg Arg Arg Gly Thr Ala Ser Leu Pro Gln Ala Gln
                165                 170                 175

Lys Pro Leu Val Phe Asp Gly Leu His Leu His Gln Ala Asp Thr Asp
            180                 185                 190

Phe Thr Gly Ile Thr Phe His Pro Asn Tyr Tyr Cys Tyr Phe Glu Arg
            195                 200                 205

Ala Arg Ser Gln Ala Leu Thr Pro Ala Val Leu Ala Asn Val Ala Glu
            210                 215                 220

Phe Ala Asn Ala Val Pro Val Ile Arg Gln Ala Arg Met Thr Phe Lys
225                 230                 235                 240

Gln Gly Ala Arg Ala Tyr Glu Thr Leu Arg Val Leu Thr Ser Ile Ala
                245                 250                 255

Leu Asp Asp Ser Gly Gly Ser Ser Ser Ser Asn Lys Tyr Val Val
            260                 265                 270

Pro Phe Glu Gln Val Leu Val Arg Arg Glu Asp Asp Lys Val Leu Val
            275                 280                 285

Glu Ala Arg Ile Glu Ile Val Phe Val Asp Gln Thr Thr Lys Leu Pro
            290                 295                 300

Cys Pro Ile Pro Asp Ala Val Ala Ala Lys Met Gln Glu Leu Phe Ala
305                 310                 315                 320
```

Val

<210> SEQ ID NO 5
<211> LENGTH: 411
<212> TYPE: DNA
<213> ORGANISM: Schizochytrium sp

<400> SEQUENCE: 5

| | | | | | |
|---|---|---|---|---|---|
| atgacggcgc | agggcggcta | cagatcggag | atgctcatgt | actatgagga | cacggacctg | 60 |
| accggagccg | tctatgcggg | caactacttc | aagtactttg | agcgcgcgcg | cgacgaggct | 120 |
| gtgggcatcg | atgtcctcaa | gacgctcatg | gacaaggagg | gcctggcttt | gtacgtgcgc | 180 |
| aaaatgggcg | agatgacctt | taaaggaggc | gccaagcacg | ccgacacgct | cgtcgtcgag | 240 |
| tcctctgtcg | aggctcccctc | ggactttcgc | cttgtgttca | agcagcgggc | atccgtcaag | 300 |
| gaccgtcccg | agacgatcat | tgtcgagacc | gatgttgagg | tcgtttgcat | cgacatgaaa | 360 |
| acgcagcgtg | tcgccaagat | cccgacgcaa | atccgggaag | cacttcgtat | c | 411 |

<210> SEQ ID NO 6
<211> LENGTH: 963
<212> TYPE: DNA
<213> ORGANISM: Schizochytrium sp

<400> SEQUENCE: 6

| | | | | | |
|---|---|---|---|---|---|
| atggctgcgc | catcgactgc | agtctgcggc | gagctgccaa | agctcgacga | ggcgcctctc | 60 |
| aaggtgtctc | gtgcacgtgg | ctacgacgcg | ctcgacgtca | aggtgtacag | agaggacaca | 120 |
| gacacagtag | ggatcgtgtt | ctatcgtaac | tttttgacct | ggtttgagcg | tggccgggaa | 180 |
| aacgcgatct | ccacagactt | tctcgcagga | ctgttcgagt | acagtggtga | ctccttcgtg | 240 |
| gtcacgcggt | ccgagcagtc | gtttcgcaag | cctgcatttt | acggcgatga | actcgaagtc | 300 |
| cgaaccattc | cttttgcaga | tgggcccttt | cgcctgcact | ttgaccagag | catctggcga | 360 |
| aagagcgaca | acacattgct | agtcgctggc | tttgtagaga | tggtcacggt | gagcagaact | 420 |
| tttcagctca | ccaaggtacc | tcagccggtg | cacgacctca | tttattactt | tgacgattgc | 480 |
| aagtcgaact | tcacctactg | cgaaaagccc | ggcgccaaga | aaaggccgct | tcggcgtaag | 540 |
| cccggggcgc | cctcttcact | tggcaaaacc | acagagcttg | acctggtcat | tcacttggcc | 600 |
| gacactgact | ttactggaat | cgcattccac | cccaactact | actgttggtt | cgagcgtgcg | 660 |
| cgctcggatt | ttctcagcaa | tgagattctt | gcacgcgcca | agaccgagtt | tcatgctgtt | 720 |
| cccgttgtgc | gcagtgcaaa | actcgcgtac | aaaaacggcg | cgaggcctgt | tgagccgctc | 780 |
| cgcattacaa | cgacgcaaga | tccgaagggc | gagcactcgg | actttgtcgt | accgattctt | 840 |
| caaaagctta | cgcgtgtctc | gaacgaccag | acgctcgtcg | aagccgtctt | tgagatgtgc | 900 |
| tttgttcatg | acaaggagcg | ccacctcgtc | aaggtcccgt | cgatcgttcg | cgatgctatt | 960 |
| gcg | | | | | 963 |

<210> SEQ ID NO 7
<211> LENGTH: 468
<212> TYPE: DNA
<213> ORGANISM: Schizochytrium sp

<400> SEQUENCE: 7

| | | | | | |
|---|---|---|---|---|---|
| atggtcatgg | tcgcggagga | gaagagggcg | cacgaggtgg | cagtacagtt | gtactatgag | 60 |
| gacacggact | tctccggctt | tgtccatcat | gccaacttcc | tgcgctactt | tgaacgcggc | 120 |

```
cgggatgaga tgattggcct gcccgttctc aaatgcttgg cccaagacga tagctcttct    180
tcttcttctg caacttcaat tggtggtggc gagcctccag tatcattgtt cgtgcataag    240
gtgcacgagt tgtcgttcaa aggtcgcgct cggcacggtg agatgctcgt ggtgcggtca    300
cgagtggtca aggaatcgga cttccgactg cgctttgcac acgaagcgtg ggtggggaac    360
acgctcgtgg cctctggatc aatggacgtg gtgttcctgt gtggctcggt cgatgcgcga    420
ttagtgaaga tccctaactc ggtcgatgtg gccttgcacg gatactat               468
```

<210> SEQ ID NO 8
<211> LENGTH: 963
<212> TYPE: DNA
<213> ORGANISM: Schizochytrium sp

<400> SEQUENCE: 8

```
atgagaatcg acgaggaggc gatacgcgtg gcagcggcgc gcgggtacga cgccttgccc     60
gtgacagtgt atcgagagtt taccgactgc ctgggcattg tgttctaccg gcactaccta    120
gcgtggtttg agcgcgggcg cgagaacgtc atctcggtgc agttcttggc ggatctgttt    180
cgcgaaacgg gggagtcgtt cgtggtgacg cgctccgagc aagtgtttaa gcgctcagcg    240
cgctatggcg accaactcga agtgcgcacc attccttttcc tggacggcga ctaccgcctc    300
ggcttcgacc agagcgtgtg gcacggcaat gagatgctcg tgcatggctt cgtggagatg    360
gtctgcgtaa gcaagagctt ccagctggcg caacaaccgg cgctcgtgcg caagctgatc    420
ggctgctttg acgagtgcac gcgcaacttc acctacgtcg gcaccaaggc ccgcatgccc    480
caaaccattc gacgacgcag aggcacggcc agtctaccac aagcacagaa gcctctagtg    540
tttgacgggc tgcacttgca ccaagcggac acagacttca caggtatcac ttttcacccc    600
aactactact gctactttga acgcgcgcgc tcgcaggcat tgactcccgc cgtattagcg    660
aacgtggctg agttcgccaa cgctgtgcca gtcatccgcc aagcccgcat gaccttcaag    720
caaggcgcga gagcgtacga gacactccgc gtgctcacat caattgctct ggatgatagc    780
ggcggcagca gcagcagcag caacaagtat gtcgtgccgt ttgagcaggt gctcgtgcga    840
agagaagacg acaaggtgct ggtggaggcg cgaatcgaga ttgtctttgt ggaccagact    900
acgaagttgc cctgcccgat tcctgacgca gtggcagcca agatgcagga gttgtttgcg    960
gta                                                                 963
```